US008016846B2

(12) United States Patent
McFarlin et al.

(10) Patent No.: US 8,016,846 B2
(45) Date of Patent: Sep. 13, 2011

(54) MICRO-RESECTING AND EVOKED POTENTIAL MONITORING SYSTEM AND METHOD

(75) Inventors: Kevin McFarlin, Jacksonville, FL (US); David Reinker, Ponte Vedra Beach, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 1086 days.

(21) Appl. No.: 11/446,520

(22) Filed: Jun. 2, 2006

(65) Prior Publication Data

US 2007/0100336 A1 May 3, 2007

Related U.S. Application Data

(63) Continuation-in-part of application No. 11/260,503, filed on Oct. 27, 2005, now Pat. No. 7,717,932.

(51) Int. Cl.
*A61B 17/32* (2006.01)
(52) U.S. Cl. ...................................... 606/170
(58) Field of Classification Search .................. 606/167, 606/170, 171, 177–180
See application file for complete search history.

(56) References Cited

U.S. PATENT DOCUMENTS 4,316,465 A * 2/1982 Dotson, Jr. ....................... 604/22
(Continued)

FOREIGN PATENT DOCUMENTS
WO 2005/074831 A2 8/2005
(Continued)

OTHER PUBLICATIONS
PCT Search Report mailed Jan. 25, 2008; 15 pgs.
(Continued)

*Primary Examiner* — S. Thomas Hughes
*Assistant Examiner* — Jonathan W Miles
(74) *Attorney, Agent, or Firm* — Dicke, Billig & Czaja, PLLC

(57) ABSTRACT

Surgical micro-resecting and evoked potential monitoring system and method. The system includes a micro-resecting instrument, handpiece, and evoked potential monitor. The instrument includes an outer tube forming a cutting window at which a cutting tip of an inner member is located. A hub assembly rotatably maintains the inner and outer members. An electrically non-conductive material covers a region of the outer tube, and wiring is connected to an exposed surface of the outer tube. The instrument defines a probe surface proximate the cutting window as part of an electrical pathway with the wiring. The hub assembly is powered by the handpiece, and the wiring is connected to the evoked potential monitor. Evoked potential monitoring is performed at the probe surface via stimulation energy delivered along the electrical pathway, and tissue/bone resection occurs with rotation of the cutting tip.

29 Claims, 13 Drawing Sheets

U.S. PATENT DOCUMENTS

| | | | | |
|---|---|---|---|---|
| 4,646,738 | A * | 3/1987 | Trott | 606/170 |
| 4,936,306 | A * | 6/1990 | Doty | 600/373 |
| 4,962,766 | A | 10/1990 | Herzon | |
| 5,026,376 | A * | 6/1991 | Greenberg | 606/96 |
| 5,284,153 | A | 2/1994 | Raymond et al. | |
| 5,284,154 | A | 2/1994 | Raymond et al. | |
| 5,474,558 | A * | 12/1995 | Neubardt | 606/79 |
| 6,139,545 | A | 10/2000 | Utley et al. | |
| 6,298,256 | B1 | 10/2001 | Meyer | |
| 6,312,392 | B1 | 11/2001 | Herzon | |
| 6,423,070 | B1 | 7/2002 | Zeppelin | |
| 6,466,817 | B1 | 10/2002 | Kaula et al. | |
| 6,523,070 | B1 | 2/2003 | Stapleton et al. | |
| 2002/0161372 | A1 | 10/2002 | Bolger et al. | |
| 2002/0169420 | A1 * | 11/2002 | Galt et al. | 604/164.12 |
| 2004/0122482 | A1 | 6/2004 | Tung et al. | |
| 2004/0260357 | A1 | 12/2004 | Vaughan et al. | |
| 2004/0260358 | A1 | 12/2004 | Vaughan et al. | |
| 2005/0096649 | A1 * | 5/2005 | Adams | 606/45 |
| 2007/0100334 | A1 | 5/2007 | McFarlin et al. | |

FOREIGN PATENT DOCUMENTS

| | | |
|---|---|---|
| WO | 2006/086367 | 8/2006 |

OTHER PUBLICATIONS

Silverstein, Otolaryngology Head and Neck Surgery article entitled "Adaptor for Continuous Stimulation (SACS) with the WR-S8 Monitor-Stimulator"; Sep. 1990; 103(3); pp. 493-496.

I. San, Turk Otolarengoloji articled "Continuous Stimulation Monitoring of the Facial Nerve"; Feb. 2001; pp. 251-254.

Silverstein; Silverstein Institute Ear Research Publication Summaries article entitled "Routine Identification of the Facial Nerve Using Electrical Stimulation During Otological and Neurotological Surgery"; www.silversteininstitute.com; Dec. 2005; 1 pg.

* cited by examiner

MICRO-RESECTING AND EVOKED POTENTIAL MONITORING SYSTEM AND METHOD

CROSS-REFERENCE TO RELATED APPLICATIONS

This application is a continuation-in-part of U.S. application Ser. No. 11/260,503, filed on Oct. 27, 2005, now U.S. Pat. No. 7,717,932 and entitled "Instrument and System for Surgical Cutting and Evoked Potential Monitoring," the teachings of which are incorporated herein by reference.

BACKGROUND

The present invention relates to surgical cutting and surgical cutting instruments. More particularly, aspects relate to surgical resecting instruments and systems capable of both high-speed cutting and electrical probing or evoked potential monitoring functions, as well as procedures utilizing such devices.

Surgical micro-resecting instruments in which an elongated, rotatable blade or cutting member is support within an elongated outer tube are well-accepted for use in various surgical cutting procedures, for example, those where access to the surgical site is gained via a narrow portal or passage. Typically, the outer tube includes a distal section forming a cutting window, with the inner member forming a cutting tip. The inner member is rotatably disposed within the outer tube, with the cutting tip being exposed at the cutting window. With rotation and/or oscillation, the cutting tip effectuates a desired surgical procedure such as cutting, resecting, abrading, shaving, etc., contacted tissue. The cutting tip is normally in the form of resecting blades/teeth or a bur.

Micro-resecting procedures (e.g., ENT) typically entail removing tissue, bone, etc., from bodily areas that are otherwise in close proximity to nerves or other delicate bodily structures. Thus, a danger exists of potentially severing or otherwise damaging nerves (or other structure) through inadvertent cutting or excessive heat. As such, conventional micro-resecting procedures oftentimes require additional steps and instruments for measuring nerve location to safely complete the procedure. Evoked potential monitoring devices are employed to periodically evaluate an intended location of the cutting tip relative to nerves. While carrying out such procedures, a surgeon may be required to sequentially remove tissue/bone with the micro-resecting instrument and then probe a cut area for nerves (or other bodily structure) using a separate implement otherwise provided with the evoked potential monitoring device. This is clearly time-consuming and thus undesirable.

SUMMARY

Some aspects in accordance with principles of the present invention relate to a method of performing a surgical micro-resecting procedure at a target site of a patient. The method includes providing a micro-resecting instrument including an outer tubular member, an inner member, a hub assembly, an electrically non-conductive material, and wiring. The outer tubular member has a lumen, a proximal section, and a distal section. The distal section forms a cutting window that is otherwise fluidly connected to the lumen. The inner member is disposed within the lumen and has a proximal portion and a distal portion. The distal portion includes a cutting tip that is positioned at the cutting window upon final assembly. The hub assembly maintains the proximal section of the outer tubular member and the proximal portion of the inner member. The electrically non-conductive material covers a region of the outer tubular member distal the hub assembly. Finally, the wiring is electrically connected to the outer tubular member. With this construction, the instrument defines a probe surface proximate the cutting window that is otherwise free of the non-conductive material. Further, an electrical pathway is established from the wiring to the probe surface. The instrument wiring is electrically connected to an evoked potential monitoring device such that an energy source of the evoked potential monitoring device is in electrical communication with the probe surface. The distal section of the outer tubular member is delivered toward the target site such that the cutting window is adjacent the target site. A stimulation energy is applied to the probe surface via the energy source and the wiring. Based upon reference to the applied stimulation energy, the evoked potential monitoring device is operated to evaluate a proximity of the probe surface relative to a bodily structure of interest. Finally, the inner member is rotated relative to the outer tubular member to perform a micro-resecting operation whereby bodily material at the target site is resected by the cutting tip within the cutting window. In some embodiments, the resecting operation and the proximity evaluation are performed simultaneously, and target site tissue is not cauterized in response to the applied stimulation energy.

Other aspects in accordance with the principles of the present invention relate to a surgical micro-resecting system including a micro-resecting instrument, a motorized handpiece, and an evoked potential monitoring device. The micro-resecting includes an outer tubular member, an inner member, a hub assembly, an electrically non-conductive material, and wiring. The outer tubular member has a lumen, a proximal section, and a distal section. The distal section forms a cutting window that is otherwise fluidly connected to the lumen. The inner member is rotatably disposed within the lumen and has a proximal portion and a distal portion. The distal portion includes a cutting tip that, upon final assembly, is positioned at the cutting window. The hub assembly maintains the proximal section of the outer tubular member and the proximal portion of the inner member. The non-conductive material covers a region of the outer tubular member distal the hub assembly. Finally, the wiring is connected to the outer tubular member, creating an electrical pathway from the wiring to a probe surface defined proximate the cutting window, with probe surface comprising a surface not otherwise covered by the non-conductive material. The motorized handpiece is coupled to the hub assembly and is configured to selectively rotate the inner tubular member relative to the outer tubular member. The evoked potential monitoring device includes an energy source that is selectively coupled to the wiring for applying a stimulation energy to the probe surface via the wiring. Further, the evoked potential monitoring device is configured to evaluate a proximity of the probe surface relative to a bodily structure of interest based upon reference to the stimulation energy. With this configuration, the system is capable of both resecting bodily material as well as evoked potential monitoring. In some embodiments, the hub assembly is configured to electrically isolate the micro-resecting instrument from the motorized handpiece. In other embodiments, the outer tubular member is curved along a length thereof distal the hub assembly. In yet other embodiments, the probe surface is defined at least in part by an exposed distal region of the outer tubular member. In yet other embodiments, the probe surface is defined at least in part by the cutting tip.

DETAILED DESCRIPTION

Figure 1:
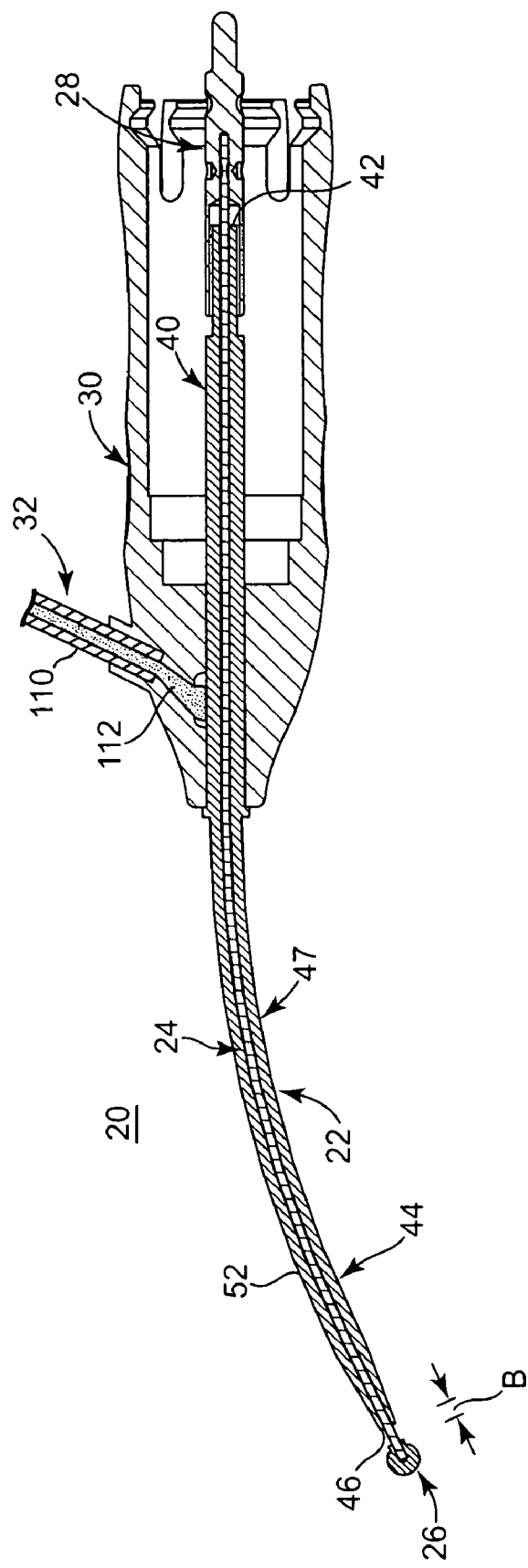
FIG. 1 is a cross-sectional view of a surgical cutting instrument in accordance with principles of the present invention.
Figure 2:
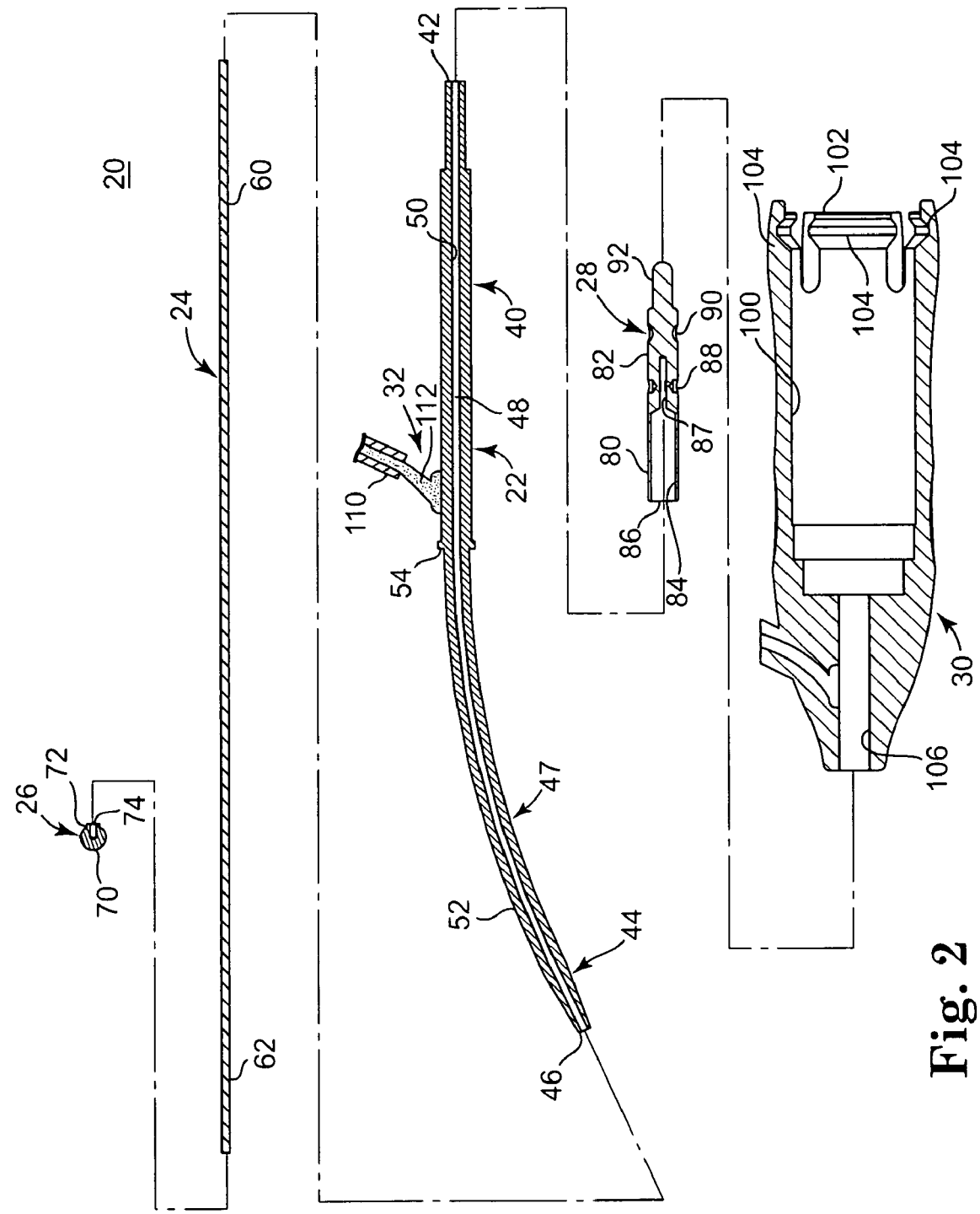
FIG. 2 is an exploded, cross-section view of the surgical cutting instrument of FIG. 1.

A surgical cutting instrument 20 in accordance with principles of the present invention is shown in FIGS. 1 and 2. The surgical cutting instrument 20 includes an outer support tube 22, an elongate drive member 24, a cutting tip 26, a coupling body (e.g., a tang) 28, a housing 30, and an electrical connector 32. In general terms, the elongate drive member 24 is coaxially disposed within the outer support tube 22. The cutting tip 26 is connected to and extends distally from the elongate drive member 24. The coupling body 28 is secured to the elongate drive member 24. The housing 30 maintains the outer support tube 22 and the coupling body 28. The electrical connector 32 delivers electrical energy from a source (not shown) to the cutting tip 26 via an electrical pathway established, at least in part, by the drive member 24, with the coupling body 28 electrically isolating the electrical pathway from components (e.g., a motor assembly) otherwise proximally mounted to the coupling body 28.

In some embodiments, a journal bearing is established between the elongate drive member 24 and the outer tube 22 upon rotation of the elongate drive member 24 relative to the outer tube 22 (e.g., via a motor assembly (not shown)). In some embodiments, the surgical cutting instrument 20 and components thereof provide one or more features that facilitate extremely high rotational speeds (on the order of 80,000 RPM), with the outer tube 22, and thus the elongate drive member 24, defining one or more curved segments where desired. U.S. application Ser. No. 10/776,835 (filed Feb. 11, 2004 and entitled "High Speed Surgical Cutting Instrument"), the teachings of which are incorporated herein by reference, describes examples of such features in accordance with one embodiment.

The outer tube 22 is an elongate tubular body, defining a proximal region 40 terminating at a proximal end 42, a distal region 44 terminating at a distal end 46, and an intermediate region 47 between the proximal and distal regions 40, 44. Further, the outer tube 22 defines a lumen 48 (best shown in FIG. 2) extending from the proximal end 42 to the distal end 46. Thus, an inner surface 50 of the outer tube 22 forms the lumen 48.

The outer tube 22 can assume a variety of longitudinal shapes. As shown at 52 in FIG. 1, in one embodiment, the outer tube 22 includes a curved segment at or along one or both of the intermediate region 47 and/or the distal region 44. In addition, the outer tube 22 is constructed to facilitate formation of a rotating journal bearing (i.e., frictional sliding journal bearing) relative to the elongate drive member 24 in the embodiment shown in FIG. 1. As will be described in greater detail below, the outer tube 22 acts as a part of an electrical pathway in some embodiments of the present invention. As such, at least a portion of the outer tube 22 is constructed of an electrically conductive material such that the outer tube 22 is capable of being in electrical communication with the elongate drive member 24 and the electrical connector 32. The outer tube 22 is also constructed of a material selected to provide the outer tube 22 with high strength, high stiffness characteristics satisfying dimensional and curvature constraints as desired. In one embodiment, the outer tube 22 is made of conventional surgical instrument materials, such as stainless steel.

Returning to FIG. 2, the elongate drive member 24 includes a proximal section 60 and a distal section 62. The elongate drive member 24 has an overall longitudinal length greater than the outer tube 22 such that, upon final assembly, the proximal and distal sections 60, 62 extend from the ends 42, 46, respectively, of the outer tube 22. The elongate drive member 24 is also constructed to be relatively thin. In particular, the thinness of the elongate member 24, in combination with the absence of a ball bearing assembly as part of the instrument 20, allows the lumen 48 to have a relatively small diameter, such that even with a preferred, minimized outer diameter, the outer tube 22 can have sufficient thickness to provide requisite stiffness when an appropriate material (e.g., 17-4 stainless steel) is selected for the outer tube 22.

In some embodiments, the elongate drive member 24 is also constructed to facilitate a rotating journal bearing relative to the outer tube 22 while maintaining structural integrity along a curved axial length. In particular, the elongate drive member 24 is formed to exhibit high strength and good fatigue characteristics. Additionally, at least a portion of the elongate drive member 24 is made of a conductive material to facilitate electrical communication between the outer support tube 22, the elongate drive member 24, and, as will be described in greater detail below, the cutting tip 26. Thus, in one embodiment, the elongate drive member 24 is formed of M2 hardened tool steel. Alternatively, other materials exhibiting the desired durability, fracture resistance, electrical conductivity, etc., can be employed for the elongate drive member 24.

Assembly of the surgical cutting instrument 20 is described in greater detail below. With respect to assembly of the outer tube 22 and the elongate drive member 24, however, a lubricant (not shown) is preferably provided along a length of the interface between the two components 22, 24 to facilitate formation of a hydrodynamic journal bearing therebetween. The elongate drive member 24 effectively "floats" relative to the outer tube 22 upon rotation of the elongate drive member 24 as it is supported by a hydrodynamic effect. As described in greater detail below, intimate contact between the outer tube 22 and the drive member 24 ensures that the desired electrical pathway is constantly maintained between the components 22, 24, such that the lubricant need not necessarily be electrically conductive. In another embodiment, the lubricant is electrically conductive and further facilitates electrical communication between the outer tube 22 and the elongate drive member 24. Thus, in one embodiment the lubricant is an electrically conductive grease lubricant, such as a lubricant available from Nye Lubricants of Fairhaven, Mass., under the trade name Nyogel 756G. However, in light of this description, it should be understood that other conductive lubricant materials can be employed.

The cutting tip 26 can assume a variety of forms, and in one embodiment includes a cutting bur 70 and an attachment end 72. The attachment end 72 is sized to receive the distal section 62 of the elongate drive member 24. To this end, the cutting tip 26 can be secured to the distal section 62 of the elongate drive member 24 via a number of known processes such as, for example, welding, braising, press-fitting, thermal shrink fitting, adhesive, etc. Alternatively, the elongate drive member 24 and the cutting tip 26 can be integrally formed such as by machining the elongate drive member 24 and the cutting tip 26 from a single piece of stock material. Regardless, the elongate drive member 24 and the cutting tip 26 should be secured in a manner to facilitate electrical communication between the two components 24, 26. As such, the cutting tip 26 is formed of electrically conductive material, such as nickel alloy materials in one embodiment. While the cutting tip 26 might include such cutting structures as small diamond burs, it should be understood that the spaces between such structures and the tissue and fluid associated with cutting operations allow an electrical interface between a cutting area (not shown) and conductive portions of the cutting tip 26. Regardless, the overall form of the cutting bur 70 can assume a variety of shapes and sizes known in the art (e.g., 2 mm fluted, 1 mm diamond, etc.). Alternatively, the cutting tip 26 can assume any other form appropriate for tissue and/or bone cutting procedures.

The coupling body 28 can assume a variety of forms but is generally configured to facilitate connection of a motor assembly (not shown) to the elongate drive member 24. As will be understood in greater detail below, some embodiments of the present invention require that the motor assembly be electrically insulated from the elongate drive member 24. In one such embodiment, the coupling body 28 is formed of a non-conductive material in order to ensure that the motor assembly is electrically insulated from the elongate drive member 24. For example, the coupling body 28 can be formed of non-conductive ceramic or plastic material, such as an Ultem® resin available from GE Plastics of Pittsfield, Mass. or other polymeric or ceramic materials exhibiting similar tensile strength. Alternatively, the coupling body 28 can be formed from metal/metal alloy with a thin, non-conductive exterior coating.

It should be understood that the motor assembly (not shown) can be of the type typically employed with surgical cutting instruments, such as electric, battery-powered, or pneumatic. One exemplary motor assembly is available from Medtronic-Xomed of Jacksonville, Fla. under the trade name Visao®. Alternatively, other types of motors or drill drive systems can be employed. In general terms, the motor assembly includes a housing maintaining a drive motor. The motor drives (e.g., rotates) a shaft or other drive mechanism that is connected to the elongate drive member 24 upon mounting of the cutting instrument 20 to the motor assembly. To this end, the drive mechanism can include a connector of a type typically employed with surgical cutting instruments that facilitates connection or coupling to the cutting device, such as a mechanical connector (e.g., the drive mechanism can include a chuck extending from a motor-driven shaft opposite the drive motor), non-contacting air-driven coupling, etc. With this in mind, the coupling body 28 of FIGS. 1 and 2 is adapted for use with a mechanical-type drive mechanism connector (e.g., chuck) for selective mounting of the coupling body 28 to the drive mechanism, with the coupling body 28 electrically isolating the drive mechanism, and thus the motor, from the elongate drive member 24.

In more specific terms, the coupling body 28 is defined by a distal portion 80 and a proximal portion 82. The distal portion 80 forms a first passage 84 extending from a distal end 86 thereof. The first passage 84 defines a diameter sized to loosely receive the proximal end 42 of the outer tube 22, serving to generally align the outer tube 22 relative to the proximal portion 82. Importantly, the distal portion 80 can rotate freely about the outer tube 22. The proximal portion 82 forms a second passage 87 extending proximally from the first passage 84. The second passage 87 is sized to receive and maintain the proximal section 60 of the elongate drive member 24. In this regard, the coupling body 28 can be further secured to the proximal section 60 of the elongate drive member 24 by a variety of techniques. For example, the coupling body 28 can be over-molded onto the elongate drive member 24. However, in one embodiment, the coupling body 28 is further secured to the proximal section 60 of the elongate drive member 24 by an epoxy, such as Loctite® M-31CL™ available from Henkel Loctite Corp. Alternatively, other epoxies or adhesives can be used.

The proximal portion 82 of the coupling body 28 forms a groove 90 and a tang 92 each adapted to facilitate coupling to the motor assembly drive mechanism (not shown), for example a chuck. The tang 92 serves as a guide surface that promotes rapid, consistent assembly of the drive mechanism to the coupling body 28. Once again, however, the coupling body 28 can assume a variety of other configurations.

Similar to the coupling body 28, the housing 30 can assume a variety of forms and is generally configured to support the outer tube 22 as well as facilitate attachment of the coupling body 28, and elongate drive member 24, to a motor assembly or "handpiece" (not shown). The instrument housing 30 is provided apart from any housing associated with the motor assembly/handpiece. The housing 30 can be formed from a non-conductive material such that the housing 30 also facilitates electrical isolation of the motor assembly from the elongate drive member 24, and in particular from the cutting tip 26, upon assembly of the cutting instrument 20 to the motor assembly. For example, in one embodiment the housing 30 is formed of a liquid crystal polymer. To this end, the housing 30 can be insert molded over the outer tube 22. Alternatively, a variety of other assembly techniques, such as gluing, welding, press fitting, thermal shrink fitting, etc., are equally acceptable. The housing 30 can incorporate a variety of features that facilitate mounting to the motor assembly. In one embodiment, the housing 30 forms a central aperture 100 having an open proximal end 102 defined by a plurality of spaced fingers 104. The central aperture 100 is sized to receive at least a portion of the motor assembly (e.g., a collet otherwise maintaining a chuck portion of the motor assembly drive mechanism), with the fingers 104 serving to capture the motor assembly within the aperture 100. In addition, or alternatively, the housing 30 can be configured to facilitate attachment to the motor assembly via snap fit, threads, interference fit, etc. Further, with the embodiments of FIGS. 1 and 2, the housing 30 defines a passage 106 fluidly connected to the aperture 100. The passage 106 is sized to maintain the outer tube 22 and can be formed during an insert molding procedure.

The electrical connector 32 includes an insulated wire 110 having an exposed end 112. For purposes of clarity, the size of the wire 110 is exaggerated in FIGS. 1 and 2. As shown in FIG. 1, the exposed end 112 is soldered to an outer surface of the outer support tube 22, with a distal portion of the wire being supported by the housing 30. However, in alternative embodiments, the electrical connector 32 can be welded, attached with a metal connector (e.g., screw), press fitted, crimped, or attached with conductive adhesive to the outer support tube 22 or integrally formed therewith. In general terms, the electrical connector 32, and in particular the wire 110, can be electrically connected to any point along a length of the outer tube 22; however, the area nearest the housing 30 or encompassed within the housing 30 is most ergonomical.

The surgical cutting instrument 20 is assembled by coaxially disposing the elongate drive member 24 within the lumen 48 of the outer tube 22. As previously described, in some embodiments a grease lubricant (not shown) is disposed along at least a portion of, preferably an entirety of, an interface between the elongate drive member 24 and the inner surface 50 of the outer tube 22. The outer tube 22 is assembled to the housing 30 as shown in FIG. 1, with the intermediate region 47 and the distal region 44 extending distal to the housing 30. As mentioned, the insulated wire 110 of the electrical connector 32 is in electrical communication with the outer tube 22 as it is soldered to a portion of the outer tube 22.

The housing 30 can be insert molded over both the outer tube 22 and a portion of the electrical connector 32 extending from the outer tube 22, with the elongate drive member 24 then being placed within the lumen 48. Additionally, in some embodiments, an exterior non-conductive coating or sleeve (not shown) is formed or provided over the outer tube 22 distal the housing 30. For example, a non-conductive sleeve (e.g., a shrink tube of polyester) can be fitted about an exterior portion of the outer tube 22 otherwise extending distally from the housing 30 to the distal end 46. As will be understood in greater detail below, the non-conductive coating or sleeve promotes the ability of the cutting tip 26 to act as an electrical probe, preventing shunting of current to surrounding tissue, bone, or other structures when a stimulation energy is applied thereto (as might otherwise occur were the metal tube 22 left exteriorly "exposed"). Additionally, various other design features of the surgical cutting instrument 20, such as material selection and the resultant journal bearing, can allow for only limited exposure of the elongate drive member 24 distal the distal end 46 of the outer tube 22, represented at B in FIG. 1. For example, the exposed length B of the elongate drive member 24 is preferably not greater than 0.1 inch (2.54 mm), and more preferably not greater than 0.05 inch (1.3 mm). In light of this disclosure, it should be understood that this limited exposure of the elongate drive member 24 (that is otherwise electrically conductive) to the environment can also promote more effective use of the cutting tip 26 as an electrical probe by reducing potential electrical shunting.

Regardless, the coupling body 28 is secured to the proximal section 60 of the elongate drive member 24, whereas the cutting tip 26 is attached to the distal section 62 of the elongate drive member 24. With this assembly, the insulated wire 110 of the electrical connector 32 is in electrical communication with the outer support tube 22, which in turn is in electrical communication with the elongate drive member 24, which in turn is in electrical communication with the cutting tip 26. This forms an electrical pathway consisting of the electrical connector 32, the outer support tube 22, the elongate drive member 24, and the cutting tip 26.

As alluded to above, the instrument 20 provides an extremely stable electrical pathway between the electrical connector 32 and the cutting tip 26. In some embodiments, intimate contact between the outer tube 22 and the elongate drive member 24 (due, at least in part, to the bend) establishes and consistently maintains the continuous electrical coupling between the two components 22, 24, such that any lubricant provided between the outer tube 22 and the drive member 24 need not be electrically conductive. In other embodiments, the use of an electrically conductive grease for the journal bearing acts to further maintain continuous electrical communication between the outer support tube 22 and the elongate drive member 24. Regardless, the journal bearing acts to maintain continuous electrical communication between the electrical connector 32 and the cutting tip 26 both at rest and during high-speed cutting operations, for example those reaching greater than 20,000 RPM, and in particular, those reaching approximately 80,000 RPM. In turn, the non-conductive coupling body 28 and non-conductive housing 30 act to insulate the motor assembly (not shown) from the electrical pathway to prevent interruption or misdirection of electrical current traveling through the electrical pathway to the cutting tip 26. This electrical isolation of the motor assembly is particularly important when the motor assembly (or handpiece) is grounded. In particular, it prevents current from being shunted away from the electrical pathway between the electrical connector 32 and the cutting tip 26.

In addition, by electrically isolating the patient-applied component (i.e., the cutting tip 26) from the motor assembly (not shown), the non-conductive coupling body 28 and housing 30 serve to prevent the conduction of any electrical or triboelectric noise from the motor assembly to the cutting tip 26 that might otherwise cause interference with other devices positioned near or at the surgical site that rely upon biosignals from the patient for proper operation. Thus, the cutting instrument 20 is highly compatible for use with other devices that amplify low-level biosigns such as EMG, EKG, EEG, ABR, etc., for the purpose of intraoperatively monitoring patient status. In fact, the electrical conductor 32 can be eliminated, with the resultant cutting instrument providing a distinct improvement over existing designs when used in conjunction with a separate patient monitoring device.

Figure 3:
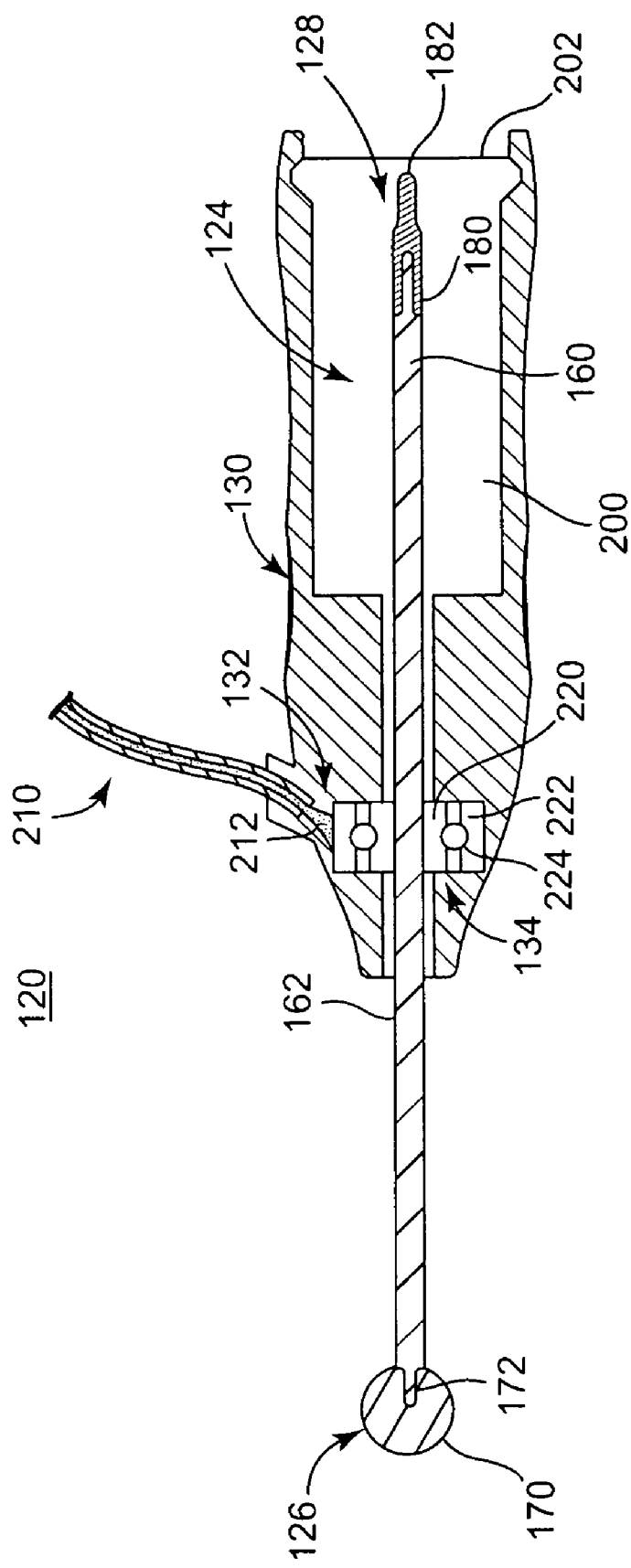
FIG. 3 is a cross-sectional view of another surgical cutting instrument in accordance with principles of the present invention.

While the surgical cutting instrument 20 has been described as providing a curved shaft configuration capable of high speed operation, in other embodiments, a more conventional straight shaft design can be employed and are capable of supporting larger shaft diameters and cutting tip diameters of 7 mm or greater (for example, for bulk bone removal procedures). For example, the surgical cutting instrument 20 can be formed with the outer tube 22, and thus the elongate drive member 24, assuming a straight or linear shape. Alternatively, FIG. 3 illustrates another surgical cutting instrument 120 in accordance with principles of the present invention that includes an elongate drive member 124, a cutting tip 126, a coupling body 128, a housing 130, an electrical connector 132, and a bearing assembly 134. The surgical cutting instrument 120 can be used as a "nose piece," similar to what is sometimes termed a "bur extender," that can be fitted on the front of a motor assembly or "handpiece" (not shown) to provide additional stability (e.g., to prevent wobble) to the elongate drive member 124 and cutting tip 126. In addition, and as described below, the surgical cutting instrument 120 is uniquely configured to establish an electrical pathway from the electrical connector 132 to the cutting tip 126.

In general terms of assembly and function, the elongate drive member 124 is coaxially disposed within the housing 130. The cutting tip 126 is connected to and extends distally from the elongate drive member 124. The coupling body 128 is secured to the elongate drive member 124 and is adapted for connection to a drive mechanism connector (not shown) of a motor assembly (not shown). The housing 130 is provided apart from the motor assembly, and maintains the electrical connector 132 and the bearing assembly 134. Thus, the housing 130 acts to maintain and support the elongate drive member 124 (as well as the cutting tip 126 secured thereto) and the bearing assembly 134. Finally, an electrical pathway is established from the electrical connector 132 to the cutting tip 126, for example via the bearing assembly 134 and the drive member 124. However, it should be noted that instead of the conductive coupling relationship shown, the cutting instrument 120 can be configured to establish an inductive or capacitive coupling to the cutting tip 126.

The elongate drive member 124 includes a proximal section 160 and a distal section 162. As shown, the elongate drive member 124 has an overall longitudinal length greater than that of the housing 130 such that upon final assembly, the distal section 162 extends from the housing 130. At least a portion of the elongate drive member 124 is formed of a conductive material in order to facilitate electrical communication with the cutting tip 126, as will be described in greater detail below. Some appropriate materials include stainless steel and tool steel materials, such as M-Series tool steels, A-Series tool steels, etc. Alternatively, other materials exhibiting the desired durability, fracture resistance, conductivity, etc., can be employed for the elongate drive member 124.

The coupling body 128 can assume a variety of forms, but is generally configured to facilitate connection of a motor assembly drive mechanism connector (not shown) to the elongate drive member 124. As a point of reference, the motor assembly (not shown) and the drive mechanism connector can assume a variety of forms (e.g., can include a chuck), as previously described in association with other embodiments. The coupling body 128 is defined by a distal portion 180 and a proximal portion 182. The distal portion 180 of the coupling body 128 is configured to facilitate coupling of the elongate drive member 124 to the coupling body 128. The coupling body 128 can be secured to the proximal section 160 of the elongate drive member 124 by a variety of techniques, such as via adhesives, male and/or female threads, overmolding the coupling body 128 over the elongate drive member 124, and others. The proximal portion 182, in turn, is configured to serve as a guide surface that promotes rapid, consistent assembly of the motor assembly drive mechanism connector (e.g., a chuck) to the coupling body 128. Once again, however, the coupling body 128 can assume a variety of other forms, as can assembly of the coupling body 128 to the elongate drive member 124 and/or to the motor assembly drive mechanism.

Similar to other embodiments previously described, the coupling body 128 is formed of a non-conductive material and serves to assist in electrically isolating the elongate drive member 124 from the motor assembly (not shown). As such, the non-conductive coupling body 128 can be formed of a variety of non-conductive materials as previously described.

The cutting tip 126 can also assume a variety of forms, including those previously described. The cutting tip 126 includes a cutting bur 170 and an attachment end 172. The attachment end 172 is configured to receive the distal section 162 of the elongate drive member 124. To this end, the cutting tip 126 can be secured to the distal section 162 of the elongate drive member 124 via a number of known methods such as, for example, welding, braising, press-fitting, thermal shrink fitting, adhesive, male and/or female threads, etc. The elongate drive member 124 and the cutting tip 126 can alternatively be integrally formed such as by machining the elongate drive member 124 and the cutting tip 126 from a single piece of stock material. Additionally, the cutting bur 170 can assume a variety of shapes and sizes known in the art (e.g., 2 mm, 1 mm diamond, etc.). Regardless, the elongate drive member 124 and the cutting tip 126 are secured together such that they are in electrical communication, as previously described in association with other embodiments.

The housing 130 can assume a variety of forms and is generally configured to maintain the elongate drive member 124, the electrical connector 132, and the bearing assembly 134, as well as facilitate mounting of the cutting instrument 120 to a motor assembly (not shown). To this end, the housing 130 can be insert molded over a portion of the electrical connector 132 and the bearing assembly 134. Alternatively, a variety of other manufacturing techniques, such as gluing, welding, press-fitting, thermal shrink fitting, etc., are equally acceptable. The housing 130 can incorporate a variety of features that facilitate assembly to the motor assembly, including those previously described. For example, in one embodiment, the housing 130 forms a central aperture 200 having an open proximal end 202 configured for attachment to a corresponding component (e.g., a collet) of the motor assembly via methods known to those of ordinary skill in the art. The central aperture 200 is sized to receive and capture at least a portion of the motor assembly. In addition, or alternatively, the housing 130 can be configured to facilitate attachment to the motor assembly via snap fits, threads, interference fit, etc. The housing 130 can be formed of a non-conductive material (e.g., a liquid crystal polymer) to assist in electrically isolating the motor assembly from an electrical pathway formed by the cutting instrument 120 as described below.

The electrical connector 132 is configured to facilitate delivery of a stimulation energy from an energy source (not shown) to the cutting tip 126 via the electrical pathway. As such, in one embodiment, the electrical connector 132 includes insulated wire 210 having an exposed end 212. As will be described in greater detail below, the insulated wire 210 can be connected to monitoring systems, such as the energy source of a nerve monitoring system (not shown). As shown in FIG. 3, the insulated wire 210 has been overmolded into the housing 130, with the exposed end 212 in contact with the bearing assembly 134. In particular, the exposed end 212 is soldered or otherwise electrically coupled (e.g., metal fastener, conductive adhesive, crimping, press fit, etc.) to the bearing assembly 134. In other embodiments, the electrical connector 132 can establish an electrical pathway to the cutting tip 126 via other means. For example, the insulated wire 210 can be connected to a wire brush, such as a beryllium brush similar to those used in motor assemblies (not shown) that is in contact with the elongate drive member 124.

In some embodiments, the bearing assembly 134 is a ball bearing-type device, and includes an inner race or ring 220, an outer race or ring 222, and rolling elements (or ball bearings) 224, all of which are formed of electrically conductive material, such as stainless steel. The bearing assembly 134 can also include a bearing retainer ring, which need not be formed of electrically conductive material in some embodiments. The bearing assembly 134, and in particular the inner ring 220, defines a bore configured to coaxially receive the elongate drive member 124. It should be noted that the elongate drive member 124 is received within the inner ring 220 with sufficient intimacy to create a continuous electrical pathway between the two components 124, 220.

From the previous description, it will be understood that the bearing assembly 134 acts as an electrical pathway between the electrical connector 132 and the elongate drive member 124, such that the two are in electrical communication. It has been surprisingly found that passivated bearings, and bearings lubricated with non-conductive lubricant, or not otherwise lubricated, can interfere with forming an electrical pathway between the electrical connector 132 and the elongate drive member 124. For example, the bearing assembly 134 is designed with small gaps between the rolling elements 224 and the races 220, 222 that allow the rolling elements 224 to effectively float in instances of time during high-speed operation. Further, the rolling elements 224 may have eccentricities that result in selective contact between the rolling elements 224, the outer ring 222, and the inner ring 220. As such, the bearing assembly 134 can include conductive grease (not shown) to fill gaps (not shown) between the rolling elements 224 and the inner ring 220 and the outer ring 222. As such, in one embodiment the bearing assembly is lubricated with a conductive grease, such as Nyogel® 756G available from Nye Lubricants of Fairhaven, Mass. As mentioned, passivation layers on the rolling elements 224, such as chromium oxide and/or nickel oxide, are often used to increase corrosion resistance and hardness of the rolling elements, but can serve to render them electrically non-conductive. As such, in one embodiment the rolling elements 224 are formed of non-passivated, stainless steel. Importantly, it has been found that by incorporating such features, the bearing assembly 134 is capable of forming a continuous electrical pathway, or continuous electrical communication, with the elongate drive member 124 and the electrical connector 132 while the cutting tip 126 is at rest and while it is turning at relatively high rotational speeds greater than 20,000 RPM, and in some embodiments at speeds approaching 80,000 RPM.

Upon final assembly, a stable electrical pathway is established from the electrical connector 132 to the cutting tip 126. Conversely, the coupling body 128, as well as the housing 130, acts to electrically insulate motor assembly (not shown) from the electrical pathway described upon mounting of the cutting instrument 120 to the motor assembly. In sum, the bearing assembly 134 includes materials and is configured such that the electrical pathway is continuously maintained during operation, without intermittent interruption, during high-speed rotation of the elongate drive member 124, such as at speeds greater than 20,000 RPM, and as high as 80,000 RPM. The non-conductive coupling body 128 electrically isolates the drive member 124 (that is otherwise part of the electrical pathway) from the corresponding component of the motor assembly drive mechanism to which the coupling body 128 is attached, whereas the non-conductive housing 130 (that otherwise is in contact with the electrical pathway) electrically isolates the cutting instruments 120 from corresponding component(s) of the motor assembly (e.g., motor assembly housing or collet) to which the instrument housing 130 is attached. Depending upon a desired distal extension of the elongate drive member 124 from the housing 130, the elongate drive member 124 can further include a non-conductive, exterior coating or sleeve to prevent shunting of electrical current away from the desired electrical pathway from the electrical connector 132 to the cutting tip 126 and/or inadvertent contact with the motor assembly.

In addition to ensuring a stable electrical pathway, the non-conductive coupling body 128 and housing 130 serve to isolate the cutting tip 126 from electrical or triboelectrical noise generated by a motor assembly (not shown) otherwise mounted to and rotating/driving the elongate drive member 124. Thus, similar to the surgical cutting element 20 (FIG. 1) previously described, in alternative embodiments, the surgical cutting instrument 120 need not include the electrical connector 132, with the resultant instrument preventing the transmission of electrical or triboelectrical noise to the cutting tip 126 in a manner that might otherwise interfere with proper operation of a separate intraoperative patient monitoring device.

Figure 4:
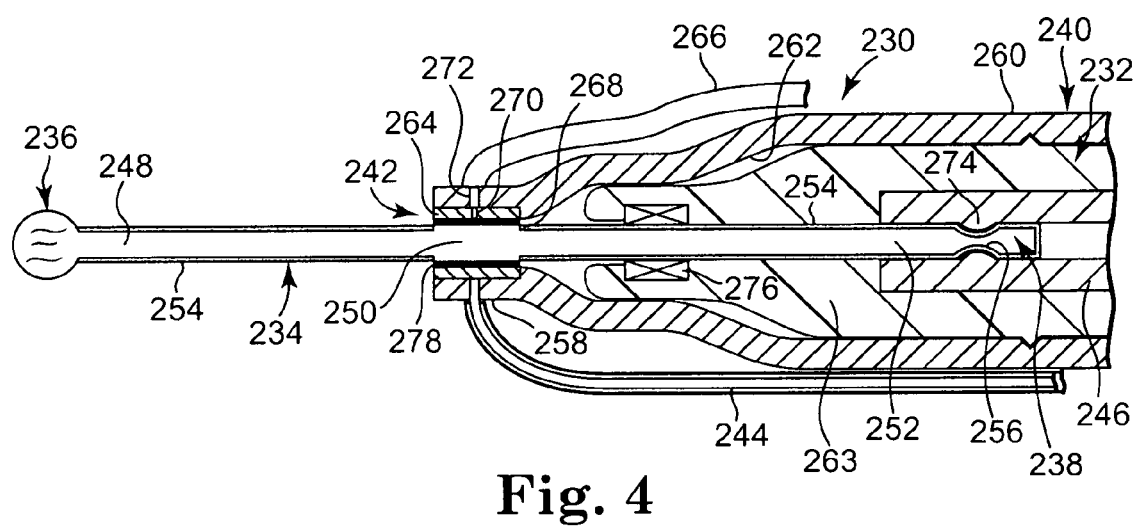
FIG. 4 is a cross-sectional view, including portions shown schematically, of another surgical cutting instrument in accordance with principles of the present invention in conjunction with a motor assembly.

A portion of another surgical cutting instrument 230 in accordance with principles of the present invention in conjunction with a portion of a motor assembly 232 is shown in FIG. 4. The instrument 230 includes an elongate drive member 234, a cutting tip 236, a coupling body 238, a housing 240, a fluid coupling assembly 242 (referenced generally), and an electrical connector 244. For ease of illustration, the drive member 234, the cutting tip 236, the coupling body 238 and portions of the motor assembly 232 are shown schematically in FIG. 4. As described below, the instrument 230 operates in a manner similar to previous embodiments, whereby the coupling body 238 is coupled to the motor assembly 232 (such as via a chuck 246) for rotating the cutting tip 236. Further, a stimulating current delivered by the electrical connector 244 flows to the cutting tip 236 via the fluid coupling assembly 242 as part of an evoked potential monitoring operation.

The drive member 234 is formed of a rigid, electrically conductive material (e.g., steel), and defines a distal portion 248, an intermediate portion 250, and a proximal portion 252. The distal portion 248 is attached to or otherwise terminates at the cutting tip 236 and thus defines an axial length or extension of the cutting tip 236 relative to the housing 240, and can assume a variety of lengths. The proximal portion 252 terminates or forms the coupling body 238. Regardless, the intermediate portion 250 can have an increased outer diameter as compared to the distal and proximal portions 248, 252 (at least in those regions immediately adjacent the intermediate portion 250), and is characterized as being exteriorly exposed as compared to the distal and proximal portions 248, 252. More particularly, an exterior of the drive member 234 is encompassed by an electrically non-conductive, insulating coating 254 (referenced generally) in all regions except the intermediate portion 250. As a point of reference, a thickness of the insulating coating 254 is exaggerated in FIG. 4 for clarity purposes. With configurations in which the drive member 234 forms the coupling body 238, the coupling body 238 is also covered by the coating 254 (it being understood that for alternative embodiments in which the coupling body 238 is formed apart from, and subsequently attached to, the drive member 234, the coupling body 238 is either comprised of an electrically non-conductive material and/or is coated with an electrically insulative covering). Conversely, with configurations in which the drive member 234 forms the cutting tip 236, the cutting tip 236 is free of the insulative coating 254. Regardless, the insulative coating 254 can take a variety of forms and can be applied in a multitude of manners. For example, the insulative coating 254 can be plastic shrink tubing, over molded plastic, etc., formed of an electrically non-conductive material.

The cutting tip 236 and the coupling body 238 can assume any of the forms previously described. Thus, the cutting tip 236 can be a bur, cutting teeth, etc. As alluded to above, the coupling body 238 can be integrally formed by the drive member 234 or provided separately. In other embodiments, however, the coupling body 238 forms a groove 256 for releasably engaging the chuck 246. Alternatively, the coupling body 238 can assume other configurations commensurate with a corresponding component of the motor assembly 232.

The housing 240 can incorporate various features previously described and is formed from, or exteriorly coated with, an electrically non-conductive material (e.g., the housing 240 can be formed of electrically insulative plastic). The housing 240 defines a distal region 258, a proximal region 260, and a central passage 262. The passage 262 along the proximal region 260 is sized to matingly receive a corresponding housing 263 (illustrated schematically) of the motor assembly 232. Conversely, the distal region 258 forms the passage 262 to be slightly greater than a diameter of the drive member 234 and is configured to maintain portions of the fluid coupling assembly 242 as described below.

The fluid coupling assembly 242 can include a conductive spacer 264 and tubing 266 fluidly connected to a source (not shown) of electrically conductive fluid. The conductive spacer 264 is formed of a hardened, electrically conductive metal and is mounted to the distal region 258 of the housing 240 about the passage 262. In some embodiments, the conductive spacer 264 is a ring or other cylindrical shape defining an internal aperture 268 (referenced generally). The internal aperture 268 has a diameter approximating an outer diameter of the intermediate portion 250 of the drive member 234 such that upon final assembly, the intermediate portion 250 is in approximate contact with the conductive spacer 264. The conductive spacer 264 can be porous and/or forms a radial opening(s) (one of which is illustrated at 270 in FIG. 4) for reasons described below.

The tubing 266 is formed of an electrically insulative material and is fluidly coupled at a proximal end (not shown) thereof to a source of electrically conductive fluid (not shown). For example, the electrically conductive fluid can be saline, etc. Regardless, a distal end of the tubing 266 is fluidly connected to the conductive spacer 264, such as via a port 272 formed in the housing 240. With this configuration, conductive fluid from the tubing 266 flows to the conductive spacer 264 and then to an interior surface thereof, due to either a porosity or other formed opening 270 in the conductive spacer 264 as previously described.

Finally, the electrical connector 244 is an insulated wire or other body capable of delivering an electrical current. The electrical connector 244 is electrically connected (e.g., welded) to the conductive spacer 264. Thus, a portion of the electrical connector 244 can extend through the housing 240 as shown.

During use, the cutting instrument 230 is mounted to the motor assembly 232 as shown. As a point of reference, the motor assembly 232 includes the chuck 246 forming an internal flange 274 nestable within the groove 256 of the coupling body 238 to facilitate engagement between the coupling body 238/chuck 246. Further, the motor assembly 232 can include bearings 276 (drawn schematically) for supporting the drive member 234 when rotated by driven rotation of the chuck 246/coupling body 238. Regardless, a stimulating current is delivered to the cutting tip 236 as part of an evoked potential monitoring operation (that may or may not occur in conjunction with cutting) by supplying a conductive fluid to the conductive spacer 264 via the tubing 266. Due to a porosity and/or other opening. 270 in the conductive spacer 264, the conductive fluid flows to an interface or spacing between the conductive spacer 264 and the intermediate portion 250 of the drive member 234. As shown, a conductive fluid film 278 is formed, electrically coupling the conductive spacer 264 and the drive member 234. Where desired, seals (not shown) can be provided distal and/or proximal the conductive spacer 264 to contain the conductive fluid at the conductive spacer 264/drive member 234 interface. Regardless, an electrical pathway is established in which a stimulating current flows from electrical conductor 244 (otherwise electrically connected to a stimulating energy source (not shown)), through the conductive spacer 264 and the conductive fluid film 278, through the drive member 234, and to the cutting tip 236. The insulative coating 254 promotes use of the cutting tip 236 as an electrical probe, preventing shunting of current to surrounding tissue. Further, the insulative coating 254 over the coupling body 238 (or other, non-conductive configuration of the coupling body 238) in conjunction with the non-conductive housing 240 electrically isolates the conductive pathway described above from the motor assembly 232 as well as from a user otherwise handling the housing 240.

Figure 5A:
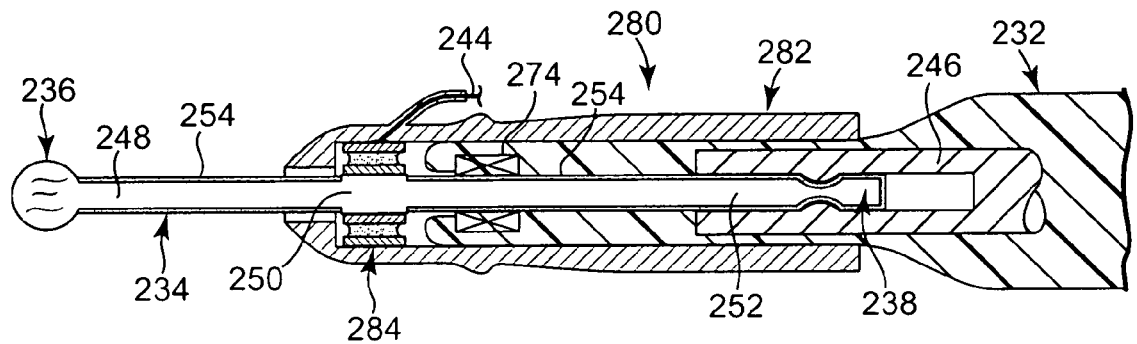
FIG. 5A is a cross-sectional view of another surgical cutting instrument in accordance with principles of the present invention in conjunction with a motor assembly.

A portion of another surgical cutting instrument 280 in accordance with the principles of the present invention in conjunction with a portion of the motor assembly 232 described above, is shown in FIG. 5A. The instrument 280 is similar in many respects to the instrument 230 (FIG. 4) previously described, with like elements having like reference numbers. With this in mind, the instrument 280 includes the elongate drive member 234, the cutting tip 236, the coupling body 238, a housing 282, an electrical coupling assembly 284 (referenced generally), and the electrical connector 244. As described below, the instrument 280 operates in a manner similar to previous embodiments, whereby the motor assembly 232 is coupled to the coupling body 238 (such as via the chuck 246) for rotating the cutting tip 236. Further, a stimulating current delivered by the electrical connector 244 (such as from a stimulating energy source (not shown)) flows to the cutting tip 236 via the electrical coupling assembly 284 as part of an evoked potential monitoring operation.

Similar to previous embodiments, the drive member 234 is formed of or coated with a rigid, electrically conductive material, and defines the distal portion 248, the intermediate portion 250, and the proximal portion 252. In this regard, the distal and proximal portions 248, 252 are encompassed or covered by the electrically non-conductive, insulating coating 254 (referenced generally) as previously described, whereas the intermediate portion 250 is exteriorly exposed.

The housing 282 is, similar to previous embodiments, formed of an electrically non-conductive material, such as plastic. In addition, the housing 282 is configured to receive and maintain the electrical coupling assembly 284, such as via a press fit. Alternatively, the housing 282 can include additional internal features that more securely receive and maintain the electrical coupling assembly 284.

Figure 5B:
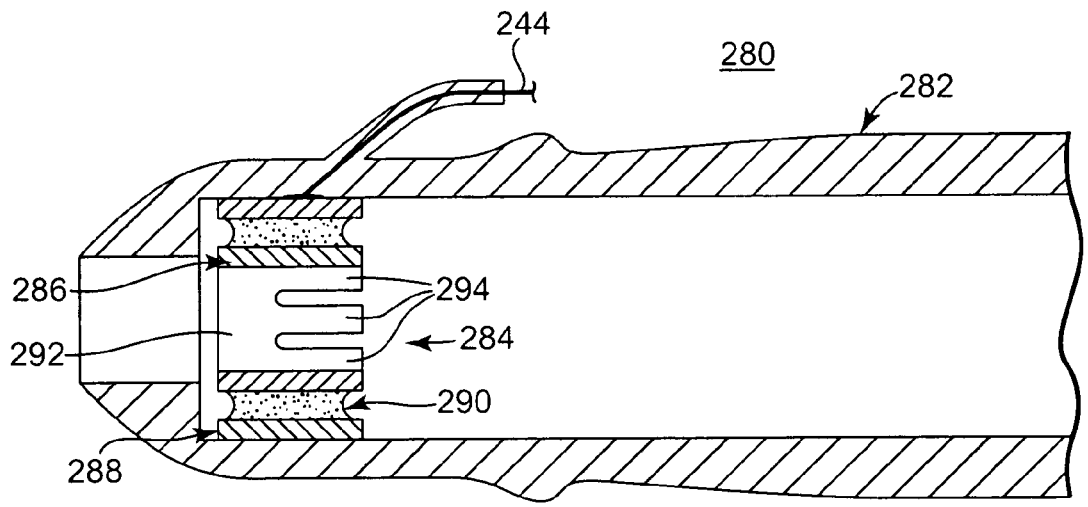
FIG. 5B is a cross-sectional view of a portion of the instrument of FIG. 5A.

With additional reference to FIG. 5B, the electrical coupling assembly 284 has a rotatable, bearing-type configuration, and includes an inner harness 286, an outer race 288, and a bearing body 290. The inner harness 286 is a generally ring-shaped body defining a base 292 and a plurality of fingers 294. The fingers 294 extend from the base 292 in a generally longitudinal fashion (relative to the longitudinal axis defined by the drive member 234), and combine to define an inner diameter approximating an outer diameter of the intermediate portion 250 of the drive member 234. Thus, upon final assembly, the fingers 294 contact and engage the intermediate portion 250 of the drive member 234. To ensure consistent, continuous contact, in one embodiment, the fingers 294 are "pre-loaded" to extend radially inwardly relative to the base 292, combining to naturally assume an inner diameter less than an outer diameter of the intermediate portion 250. Regardless, the inner harness 286 is formed of an electrically conductive metal, such as steel. The outer race 288 is similarly formed of a conductive metal, and is sized for securement to the housing 282 (e.g., press fit). Finally, the bearing body 290 is also electrically conductive, and is adapted to facilitate rotation of the inner harness 286 relative to the outer race 288. For example, the bearing body 290 can be a ferro-fluid bearing. In addition, or as an alternative, the bearing body 290 can include one or more ball bearing(s) formed of an electrically conductive material (e.g., steel). Regardless, the electrical connector 244 includes an insulated wire electrically coupled (e.g., welded) to the outer race 288, and thus, can extend through a thickness of the housing 282. With this configuration, an electrical pathway is established from the electrical connector 244 to the cutting tip 236 via the electrical coupling assembly 284 and the drive member 234.

Returning to FIG. 5A, during use the instrument 280 is connected to the motor assembly 232. For example, the chuck 246 (shown schematically) is connected to the coupling body 238, with the bearings 274 (shown schematically) supporting the drive member 234 as previously described. Rotation of the chuck 246 causes the cutting tip 236 to rotate as part of a cutting operation. In addition, the instrument 280 can be employed to perform an evoked potential monitoring operation apart from and/or simultaneously with tissue cutting. A stimulating current is delivered via the electrical connector 244 to the electrical coupling assembly 284. In particular, the stimulating current is delivered to the outer race 288 which in turn conducts the current to the inner harness via the bearing assembly 290. Intimate contact between the inner harness 286 and the drive member 234 (regardless of whether the drive member 234 is rotating) conducts the applied current to the cutting tip 236. Once again, the insulative coating 254 prevents shunting of the current distal the housing 282, such that the current is focused upon the cutting tip 236. In addition, the insulative coating 254 (and/or other non-conductive features associated with the coupling body 238) and the housing 282 combine to insulate the motor assembly 232 from the current, as well as from a user otherwise handling the housing 282. In some embodiments, the housing 282/electrical coupling assembly 284 serves as a re-usable device, and thus can be repeatedly employed with a variety of other drive members 234 (and thus, cutting tip 236 and coupling body 238) configurations.

Figure 6:
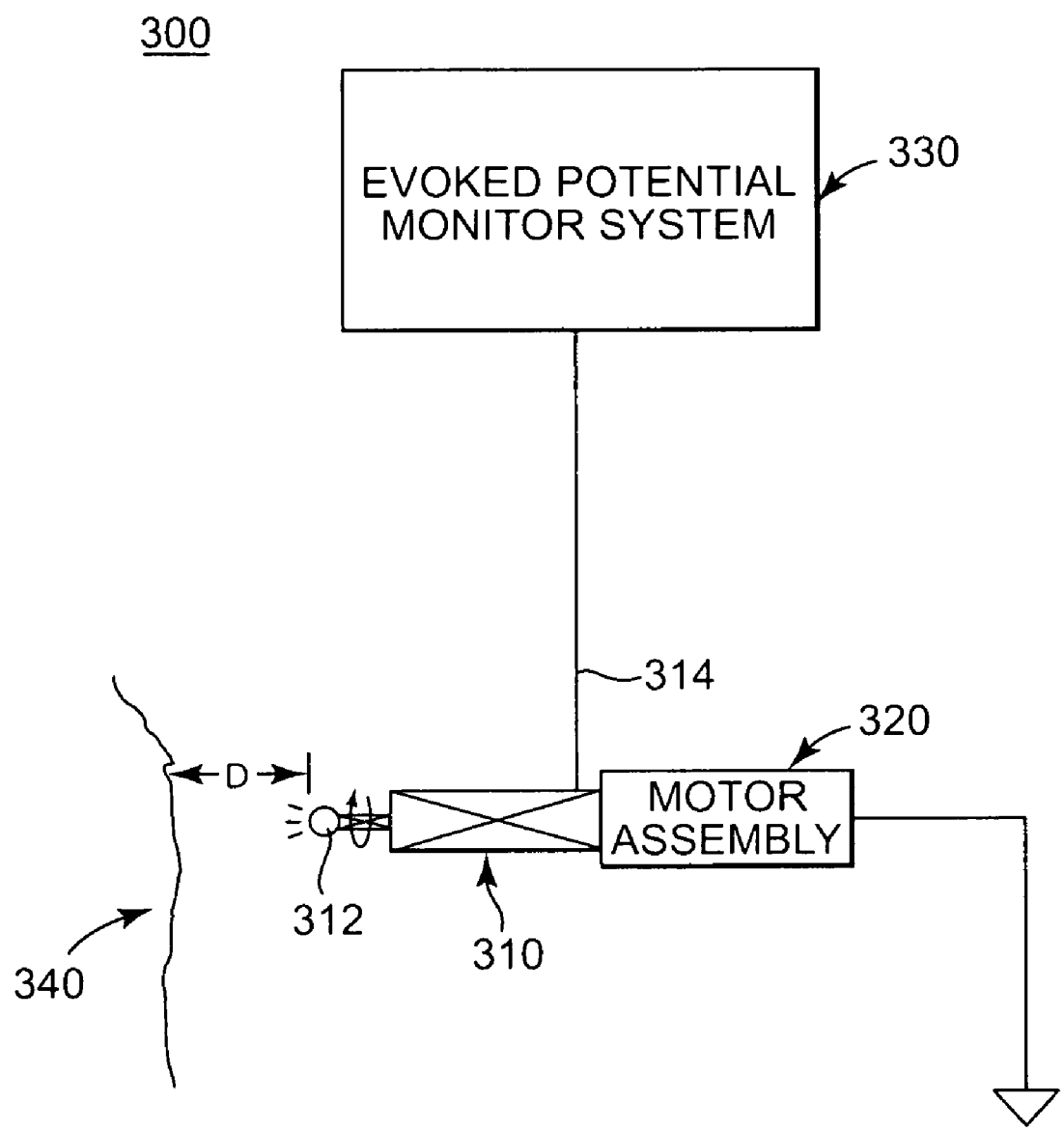
FIG. 6 is a schematic illustration of a surgical cutting system in accordance with principles of the present invention.

Regardless of an exact form of the surgical cutting instrument, a surgical cutting system can be provided in accordance with principles of the present invention. For example, FIG. 6 illustrates schematically a surgical cutting system 300 in accordance with principles of the present invention. The surgical cutting system 300 includes a surgical cutting instrument 310, a motor assembly 320, and an evoked potential monitor (or monitoring) system or device 330. It has been discovered that the sequential and separate process of probing then cutting, or vice-versa, as has been required in the past, is an area of potential improvement addressed by the surgical cutting system 300, resulting, for example, in an early warning system for surgeons, alerting them to potential iatrogenic injury to neural tissue. The simultaneous cutting and probing procedure described below is safer for the patient (as compared to the conventional technique of alternating cutting and probing) as the surgeon is no longer required to manually estimate the appropriate depth of cut between probing operations, and overall procedure time is reduced.

The surgical cutting instrument 3 10 can be of a similar design to the surgical cutting instruments 20 (FIG. 1), 120 (FIG. 3), 230 (FIG. 4), or 280 (FIG. 5A), previously described, and generally includes a cutting tip 312 and an electrical connector 314, with the electrical connector 314 being electrically connected to the cutting tip 312 via an electrical pathway established by the cutting instrument 310 as previously described. The motor assembly 320 can assume any known form, and though shown schematically, generally includes a housing, a motor and a drive mechanism/connector, with the surgical cutting instrument 310 and the motor assembly 320 adapted for mounting to one another as previously described. Regardless, the motor assembly 320 and the surgical cutting instrument 310 are assembled such that motor assembly 320 drives (e.g., rotates) the cutting tip 312 in order to perform a cutting operation. Notably, as described above, the motor assembly 320 is electrically isolated from the cutting tip 312 and the electrical pathway upon mounting of the cutting instrument 310 to the motor assembly 320.

The evoked potential monitor system 330 is a nerve integrity monitoring system, such as a NIM-Response® 2.0 nerve integrity monitoring system available from Medtronic-Xomed, Inc. of Jacksonville, Fla. In general terms, the evoked potential monitor system 330 is adapted to indicate when an energized probe, for example the cutting tip 312, is proximate a nerve 340 (shown schematically) during a surgical cutting procedure. For example, the evoked potential monitor system 330 can include a patient interface console maintaining circuitry and related equipment, the console being capable of providing a stimulating energy or current to a probe via a stimulating energy source provided as part of the system 330. In addition, electrodes (not shown) are placed on or in muscles that are enervated by nerves in proximity to the expected cutting area, and are electrically coupled to the interface console. In this manner, the electrodes signal a response to the patient interface console's internal equipment (e.g., processor) when a stimulating current enervates a nerve of concern. The evoked potential monitor system 330 can also include alarms or other indicators as known in the art. Regardless, the electrical connector 314 is in electrical communication with both the evoked potential monitor system 330 and the cutting tip 312 (via the electrical pathway). In this manner, the cutting tip 312 serves as an electrical probe in conjunction with the evoked potential monitor system 330 when energized via the electrical connector 314.

During use, the evoked potential monitor system 330 prompts delivery (preferably continuous delivery) of a stimulating energy (e.g., current) through the electrical connector 314 to the cutting tip 312 via the electrical pathway established by the cutting instrument 310. The previously described surgical cutting instruments 20 (FIG. 1), 120 (FIG. 3), 230 (FIG. 4), 280 (FIG. 5A) are several examples of instruments capable of ensuring that the stimulating energy is continuously delivered to the cutting tip 312. Properly placed patient electrodes (not shown) provide the evoked potential monitor system 330 with information indicative of a proximity of the cutting tip 312 to the nerve 340 in response to the applied stimulating current. For example, based on a comparison of the applied stimulating current with the signaled information from the patient electrodes, the evoked potential monitor system 330 can detect, and/or provide the user with information indicative of, the energized cutting tip 312 being at or within a distance D of the nerve(s) 340 of concern. The motor assembly 320, otherwise electrically isolated from the delivered stimulation energy, is simultaneously powered to rotate the cutting tip 312. Thus, simultaneous or substantially concurrent bone or tissue cutting and nerve probing functions can be performed by the system 300. Further, evoked potential monitoring can be performed via the cutting instrument 310 with the motor assembly 320 deactivated (i.e., "off" or not otherwise driving the cutting instrument 310).

Figure 7:
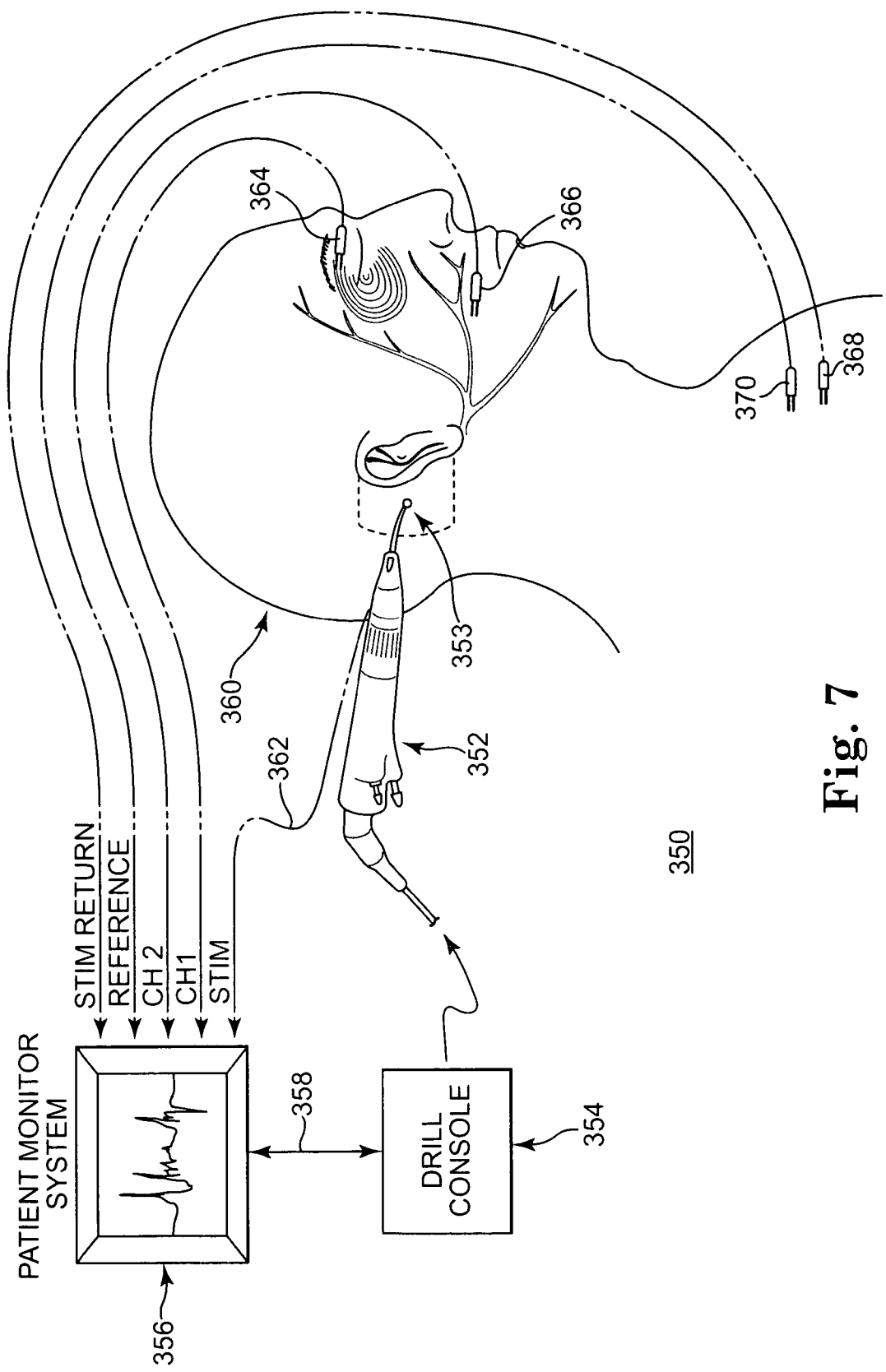
FIG. 7 is a schematic illustration of another surgical cutting system in accordance with principles of the present invention.

In a related surgical cutting system 350 shown in FIG. 7, a surgical cutting instrument 352 having a cutting tip 353 is again powered by a motor assembly (illustrated schematically in FIG. 7 as part of the cutting instrument 352). The surgical cutting instrument 352 can assume any of the forms previously described. The cutting instrument/motor assembly 352 is electronically coupled to a surgical drill console 354, such as an XPS® console (Medtronic-Xomed, Inc., of Jacksonville, Fla.), having internal circuitry for controlling power delivered to the motor assembly 352. The system 350 further includes a patient monitor system 356 such as an evoked potential monitor system as previously described or a surgical navigation platform such as an image guidance system available under the trade name LandmarX® Element IGS System from Medtronic-Xomed, Inc., of Jacksonville, Fla. Regardless of an exact configuration, a communication link 358 (wired or wireless connection) is established between the surgical drill console 354 and the patient monitoring system 356, with the patient monitor system 356 being adapted (e.g., processor operating pursuant to appropriate programming) to prompt the surgical drill console 354 to disable the motor assembly 352 via a signal delivered through the communication link 358.

More particularly, the patient monitoring system 356 is adapted to monitor a patient 360 during a surgical procedure involving the surgical cutting instrument 352. Patient monitoring can include evoked potential monitoring as previously described (e.g., a wire 362 can provide a stimulating current from the patient monitor system 356 to the cutting instrument 352), or can be any other appropriate type of monitoring (e.g., image guidance). For example, in some embodiments, the patient monitor system 356 includes EMG electrodes 364, 366 ("CH 1" and "CH 2"), along with a stimulation return path electrode 368 ("STIM RETURN") and a reference electrode 370 ("REFERENCE"). The EMG electrodes 364, 366 are placed in muscles innervated by the nerves of concern. The return path electrode 368 provides a return path for the stimulation current delivered by the cutting tip 353 for embodiments in which the delivered simulation current is an isolated output that is not Earth referenced (and therefore requires its own isolated return). The reference electrode 370 provides a common reference between the patient 360 and the patient monitor system 356 (required to center the EMG signal within the input range of the recording amplifiers). The return path and reference electrodes 368, 370 can be placed at a variety of locations on the patient 360, such as the sternum, shoulder, forehead, etc. Regardless, upon detecting or otherwise determining that the cutting tip 353 is proximate critical anatomy (e.g., nerve) of the patient 360, the patient monitor system 356 is adapted to deliver a disabling signal to the surgical drill console 354, prompting powering off of the cutting instrument/motor assembly 352. Thus, the system 350 effectively provides an automatic "kill-switch" to further ensure patient safety.

Figure 8:
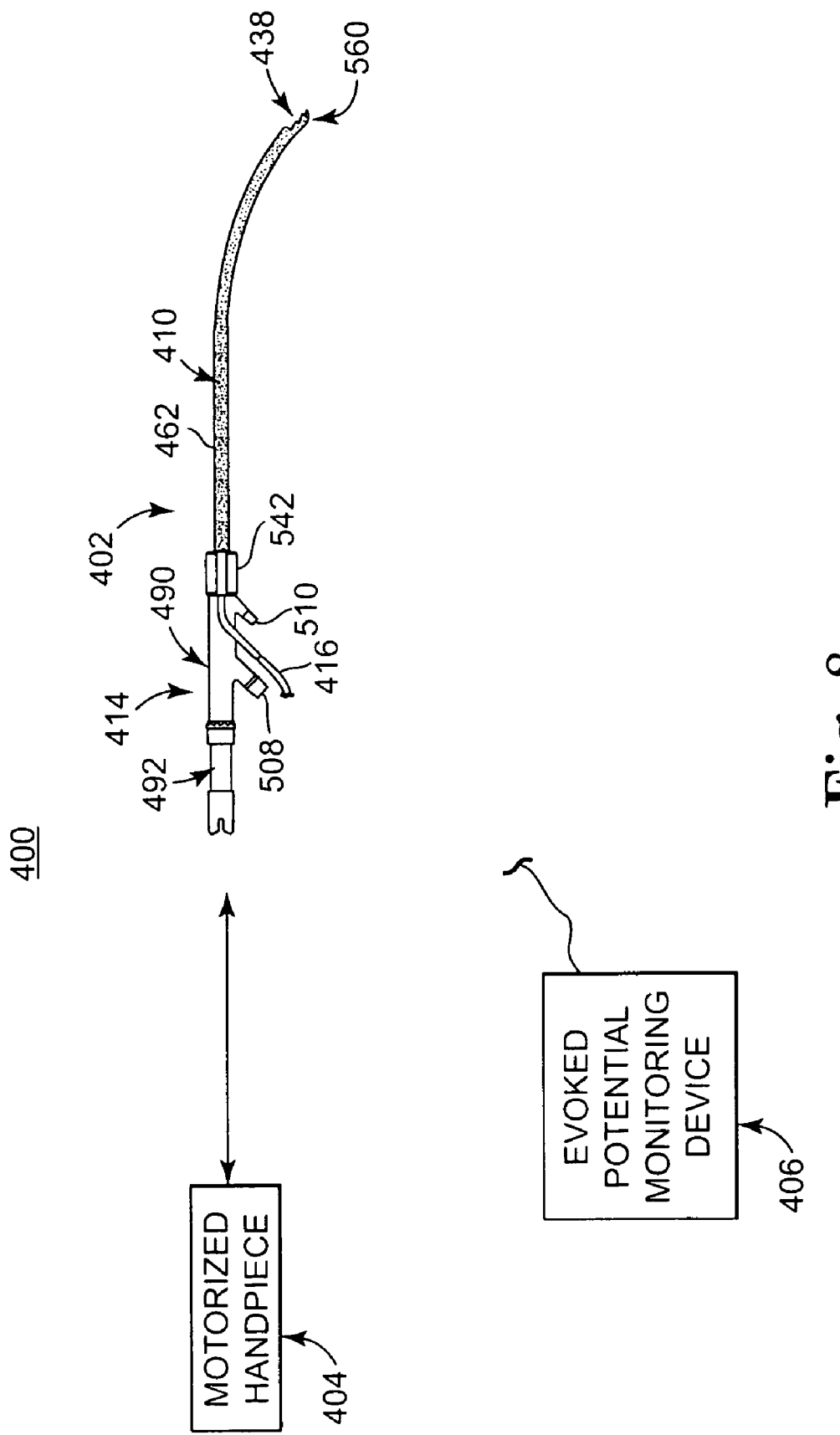
FIG. 8 is a schematic illustration, with portions shown in block form, of another surgical cutting system in accordance with principles of the present invention incorporating a surgical micro-resecting instrument.

Another surgical cutting system 400 in accordance with principles of the present invention is illustrated schematically in FIG. 8. The system 400 includes a surgical cutting instrument 402, a motorized handpiece or motor assembly 404, and an evoked potential monitoring device 206. In general terms, the system 400 is highly similar to the systems 300, 350 previously described in that the motorized handpiece 404 operates the instrument 402 to perform a cutting procedure (as described below), along with the evoked potential monitoring device 406 utilizing the instrument 402 to perform evoked potential probing procedures. With the configuration of FIG. 8, however, the surgical instrument 402 is a micro-resecting instrument that, in some embodiments, incorporates the features described below.

Figure 9:
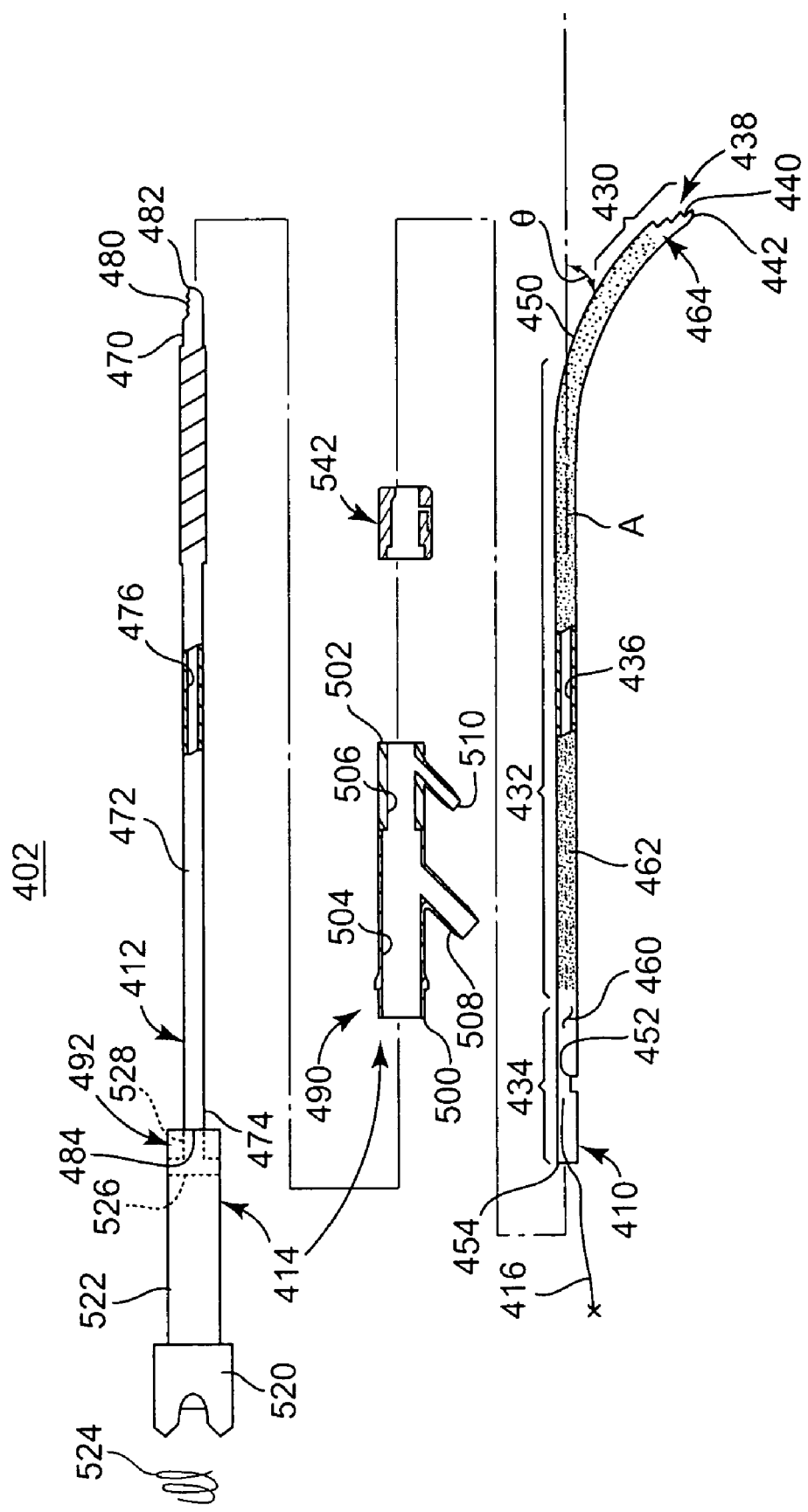
FIG. 9 is an exploded view of the surgical micro-resecting instrument of FIG. 8.
Figure 10:
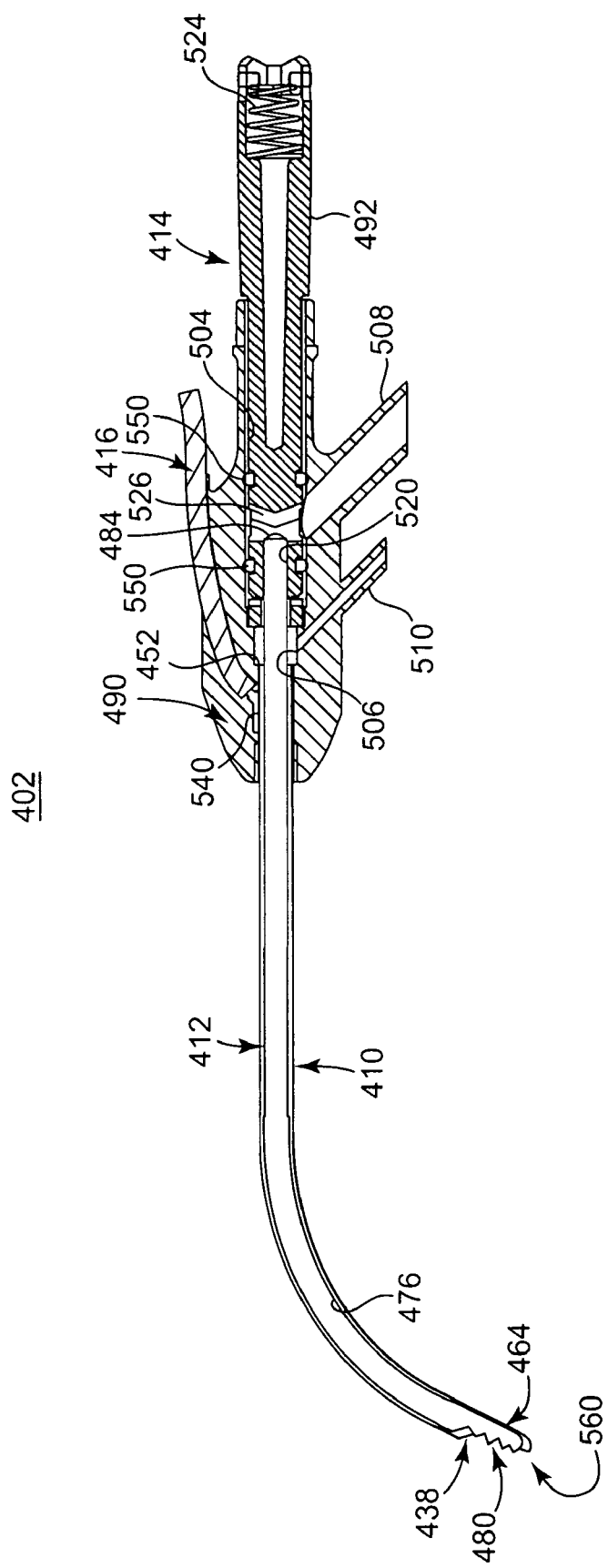
FIG. 10 is a cross-sectional view of the surgical micro-resecting instrument of FIG. 9.

With additional reference to FIGS. 9 and 10, in some embodiments, the surgical micro-resecting instrument 402 includes an outer tubular member 410, an inner member 412, a hub assembly 414, and wiring/cable (or electrical connector) 416. The components 410-416 are described in greater detail below. More generally, the inner member 412 is coaxially disposed within the outer tubular member 410. The hub assembly 414 maintains the inner member 412 relative to the outer tubular member 410 in a manner that allows the inner tubular member 412 to rotate and/or oscillate relative to the outer member 410. One or both of the outer and inner members 410, 412 provides a probe surface (as described below) at which a stimulation energy is applied to a patient as part of an evoked potential evaluation procedure initiated by the evoked potential monitoring device 406 via the wiring 416.

As best shown in FIG. 9, the outer tubular member 410 is formed as an elongated tube, defining a distal section 430, an intermediate section 432, and a proximal section 434. A lumen 436 extends from the distal section 430 to the proximal section 434. Finally, the proximal section 434 forms an open cutting window 438 (referenced generally in FIG. 9) that is otherwise fluidly connected to the lumen 436. The proximal section 434 can form a cutting surface or edge 440 (referenced generally in FIG. 9) about at least a portion of the cutting window 438. For example, with the configuration of FIG. 9, several teeth are formed on either side of the cutting window 438. Regardless, the cutting surface 440 defines a perimeter of the cutting window 438 such that the cutting window 438 is open to the lumen 436. With this configuration, then, the distal section 430 terminates at a distal end 442 that is otherwise distal the cutting window 438 (and thus is closed relative to the lumen 436). The closed distal end 442 serves to distally shield a cutting surface of the inner member 412 upon final assembly, whereas the cutting window 438 exposes the surface. In some embodiments, an exterior surface of the closed distal end 442 is curved.

The intermediate section 432 extends from the distal section 430 to the proximal section 434 and forms a bend 450. The distal section 430 can be linear in longitudinal extension. Thus, due to the bend 450, the distal section 430 extends at or forms a bend angle Θ relative to a longitudinal axis A of the proximal section 434. The bend angle Θ is selected to facilitate desired positioning of the distal section 430 (and thus of the cutting window 438) at a target site as part of a particular surgical procedure. With this in mind, the bend angle Θ is in the range of 0°-120° (i.e., in some embodiments where the bend angle Θ is 0°, the intermediate section 432 is linear along an entirety thereof). Along these same lines, two or more bends can be provided along a length of the outer tubular member 410 (e.g., along one, two, or all of the sections 430-434). Further, the bend 450 can be formed at a longitudinal position varying from that shown in FIGS. 8-10.

The proximal section 434 is adapted for connection to the hub assembly 414 as described below. In some embodiments, the proximal section 434 forms an irrigation inlet or opening 452 adjacent the proximal end 454. The inlet 452 is fluidly open to the lumen 436 and, as described below, establishes a fluid connection between the lumen 436 and a corresponding component of the hub assembly 414. Alternatively, the proximal section 434 can assume a variety of other forms.

The outer tubular member 410 can be formed of a hardened, surgically-safe material, capable of supporting the inner tubular member 412 at high rotational/oscillation speeds (e.g., oscillation speed on the order of 5,000 rpm), while maintaining the bent shape illustrated. In addition, the material selected for the outer tubular member 410 is electrically conductive. Thus, for example, the outer tubular member 410 can be formed of 304L stainless steel; although a multitude of other materials are equally acceptable. Regardless, an outer surface 460 (referenced generally in FIG. 9) of the outer tubular member 410 is coated or covered with a dielectric insulation or non-conductive material (shown generally at 462 by stippling in FIGS. 8 and 9) along the intermediate section 432 and at least a portion of the distal section 430. The non-conductive coating 462 material can be a polyolefin coating, but other known dielectric or non-conductive materials can also be employed (e.g., can be a non-conductive shrink-wrap material applied to the outer tubular member 410). In some embodiments, the outer surface 460 along the proximal section 434 is preferably free of the non-conductive coating 462 to provide a contact point for the wiring 416. In addition, a distal region 464 of the distal section 430 can also be free of the non-conductive coating 462. As described below, the exposed distal region 464 defines a surface from which electrical energy can be conducted. In some embodiments, the exposed distal region 464 encompasses the cutting window 438, while in other embodiments, the cutting window 438 is covered by the non-conductive material 462.

The inner member 412 is, in some embodiments, an elongated tube and thus can be referred to as an "inner tubular member," it being understood that the inner member 412 is not limited to a tubular design. Regardless, the inner member 412 defines a distal portion 470, an intermediate portion 472, and a proximal portion 474. Further, the inner member 412 can define a central lumen 476 extending from the distal portion 470 to the proximal portion 474. The inner member 412 is sized to be coaxially received within the outer tubular member 410, with the proximal portion 474 adapted for mounting to the hub assembly 414 as described below.

Similar to the outer tubular member 410, the inner tubular member 412 is formed of electrically conductive material(s) (e.g., metal). While, as described below, the portions 470-474 need not be constructed identically, each portion 470-474 is electrically conductive such that when assembled to the outer tubular member 410, electrical energy can be conducted from the outer tubular member 410 to the inner member 412. At least the intermediate portion 472 can have a flexible construction such that the inner member 412 will assume the shape of the outer tubular member 410 (and in particular the bend 450) upon insertion of the inner member 412 within the outer tubular member 410. For example, the intermediate portion 472 can be or includes a wound coil(s) or reinforced tube(s) (e.g., inner and outer spiral wraps assembled over a spiral cut formed in the inner member 412), series of laser cut/dovetailed sections, etc. (it being understood that the intermediate section 472 is illustrated generally in FIG. 9). Regardless, while the portions 470-474 may have differing constructions (e.g., the distal and proximal portions 470, 474 are metal tubes, whereas the intermediate portion 472 is a wound metal coil), the inner member 412 has an overall construction capable of maintaining structural integrity when rotated and/or oscillated at high speeds (e.g., oscillation speeds on the order of 5,000 rpm).

The distal portion 470 forms or includes a cutting tip 480. The cutting tip 480 is fluidly open to the central lumen 476 (e.g., serves as a mouth to the central lumen 476), and is defined by or forms a plurality of teeth 482 (commonly known as a micro-resecting "blade"). With this configuration, the cutting tip 480/teeth 482 provide a micro-resecting surface alone or in combination with the cutting surface 440 associated with the outer tubular member 410 as is known in the art. Thus, the cutting tip 480 can assume a verity of forms.

A proximal end 484 of the inner tubular member 412 is also open to the lumen 476 in some embodiments, and provides an aspiration pathway for aspirating material from the cutting tip 480 to the proximal end 484 via the lumen 476.

Regardless of exact configuration, at least a majority of an inner diameter of the outer tubular member 410 can be slightly larger than an outer diameter of the inner member 412 so as to establish a gap between the two components 410, 412 upon final assembly. As described in greater detail below, this gap establishes an interior irrigation pathway by which an irrigation fluid can be delivered to the cutting window 438.

The hub assembly 414 can include a first hub 490 and a second hub 492. One exemplary description of the hubs 490, 492 is provided below. In more general terms, however, the hub assembly 414, and in particular the hubs 490, 492, are configured to retain the inner and outer members 410, 412 relative to one another, as well as to provide a mechanism for rotating/oscillating the inner member 412 via the motorized handpiece 404 (FIG. 8). In addition, the hub assembly 414 is configured to electrically isolate the inner and outer members 410, 412 from the motorized handpiece 404, and thus serves as an electrically non-conductive coupler. For example, each of the first and second hubs 490, 492 can be formed of a rigid, electrically non-conductive material, such as ABS plastic.

With the above in mind, the first hub 490 can serve as an outer hub and is configured to retain the outer tubular member 410, as well as the inner member 412 and the second hub 492. In this regard, the first hub 490 is an elongated body defining a proximal end 500, a distal end 502, a proximal passage 504, a distal passage 506, an aspiration port 508, and an irrigation port 510. The proximal passage 504 extends from the proximal end 500 and is sized to receive a portion of the second hub 492. Further, the proximal passage 504 is fluidly connected to the aspiration port 508. The distal passage 506 is fluidly connected to, and extends from, the proximal passage 504, terminating at the distal end 502. The irrigation port 510 is fluidly connected to the distal passage 506. As described below, the distal passage 506 is sized in accordance with an outer diameter of the outer tubular member 410 such that the outer tubular member 410 is coupled to the first hub 490 upon final assembly. Further, a position of the irrigation port 510 corresponds with the position of the irrigation slot 452 formed by the outer tubular member 410 such that upon final assembly, the irrigation inlet 452 is aligned with the irrigation port 510. As described below, then, the first hub 490 provides both an irrigation pathway for internal irrigation and also an aspiration pathway for the aspiration of fluids and other bodily material during use.

The second hub 492 serves as an inner, rotating hub and is an elongated body defining a proximal segment 520 and a distal segment 522. The proximal segment 520 is configured to releasably secure the surgical micro-resecting instrument 402 to the motorized handpiece 404, and may include a coupling device such as a spring 524. The distal region 522 is sized to be slidably received within the proximal passage 504 formed by the first hub 490, and forms a radial passage 526 and a longitudinal passage 528. The longitudinal passage 528 is sized to receive and maintain the proximal end 454 of the inner member 412. The radial passage 526 is in fluid communication with a longitudinal passage 528, and is generally aligned with the aspiration port 508 upon final assembly. With this configuration, then, fluids and other bodily materials can be drawn through the central lumen 476 of the inner member 412 via the aspiration port 508.

The wiring 416 is akin to the electrical connector 132 (FIG. 1) previously described and thus can be an insulated wire having a terminal end 540 (FIG. 10). The terminal end 540 is electrically connected to the outer tubular member 410, such as by soldering or otherwise connecting (e.g., a metal fastener, conductive adhesive, crimping, press-fit, etc.) to the "exposed" outer surface 460 along the proximal section 434 of the outer tubular member 410. With the configurations of FIGS. 8 and 9, an electrically non-conductive cap 542 is provided to encompass the terminal end 540/outer tubular member 410 interface. The non-conductive cap 542 can be permanently assembled to the outer tubular member 410, or can be provided as a disposable component used to convert an existing surgical micro-resecting instrument to a stimulating probe by securing electrical wiring to an outer surface of the instrument. In other embodiments, the wiring 416 extends through a passage in the first hub 490 (e.g., as part of an over-molding manufacturing step) as shown in FIG. 10, such that the cap 542 can be eliminated.

Assembly of the micro-resecting instrument 402 includes electrically coupling the terminal end 540 of the wiring 416 to the outer tubular member 410. The proximal section 434 of the outer tubular member 410 is then assembled to the distal end 502 of the first hub 490. As shown in FIG. 10, upon final assembly the irrigation inlet 452 of the outer tubular member 410 is aligned with the irrigation port 510 of the first hub 490.

The proximal portion 474 of the inner member 412 is assembled to the distal segment 522 of the second hub 492. The inner member 412 is then coaxially disposed within the outer tubular member 410. In this regard, the distal segment 422 of the second hub 492 is coaxially placed within the first hub 490. In one embodiment, seal rings 550 (FIG. 10) are positioned proximal and distal the radial passage 526 to seal the radial passage 526 of the second hub 492 relative to the aspiration port 508 of the first hub 490. The seal rings 550 also seal the aspiration port 508 relative to the irrigation port 510. In alternative embodiments, one or both of the aspiration or irrigation features can be eliminated; accordingly the inner member 412 need not be a tube and instead is a solid shaft.

Upon final assembly, an electrical pathway is established by the micro-resecting instrument 402 from the wiring 416 to a probe surface 560 (referenced generally in FIGS. 8 and 10) via the electrically conductive construction of the outer tubular member 410. The probe surface 560 is defined, in one embodiment, at least in part by the exposed distal region 464 of the outer tubular member 410. The outer tubular member 410 is electrically insulated distal the hub assembly 414 by the non-conductive material 462 (it being understood that in the cross-sectional view of FIG. 10, the non-conductive material 462 is not visible due to its highly thin nature in one embodiment) except at the exposed distal region 464 such that electrical energy applied to the outer tubular member 410 (such as part of an evoked potential probing procedure) conducts away from the outer tubular member 410 only at the exposed region 464. In addition, the electrical pathway can also include conduction of electrical energy to the cutting tip 480 of the inner tubular member 410, such that the probe surface 560 can further include the cutting tip 480. For example, the inner and outer members 410, 412, are normally in intimate, metal-to-metal contact due to, in part, the bend 450. Electrical energy conducted from the wiring 416 to the outer tubular member 410 is similarly conducted to the inner member 412, and thus the cutting tip 480. Where desired, this electrical conduction can be further enhanced or ensured via the addition of an electrically conductive grease (not shown) disposed between the inner and outer tubular members 410, 412. With the above in mind, in some embodiments, the probe surface 560 is defined by the exposed distal region 464 alone; in other embodiments by the cutting tip 480 alone; and in yet other embodiments by a combination of the exposed distal region 464 and the cutting tip 480. Regardless of exact construction, the probe surface 560 is in close proximity to, or includes, the cutting window 438 and thus is indicative of a location of the cutting window 438/cutting tip 480.

In addition to the electrical pathway described above, the micro-resecting instrument 402 can provide an aspiration pathway from the aspiration port 508 to the cutting tip 480 of the inner member 412 via the central lumen 476 thereof. Similarly, an irrigation pathway is provided from the irrigation port 510 to the cutting window 438 via a spacing between the inner and outer members 410, 412. Alternatively, the aspiration pathway and/or the irrigation pathway can be eliminated.

Figure 11:
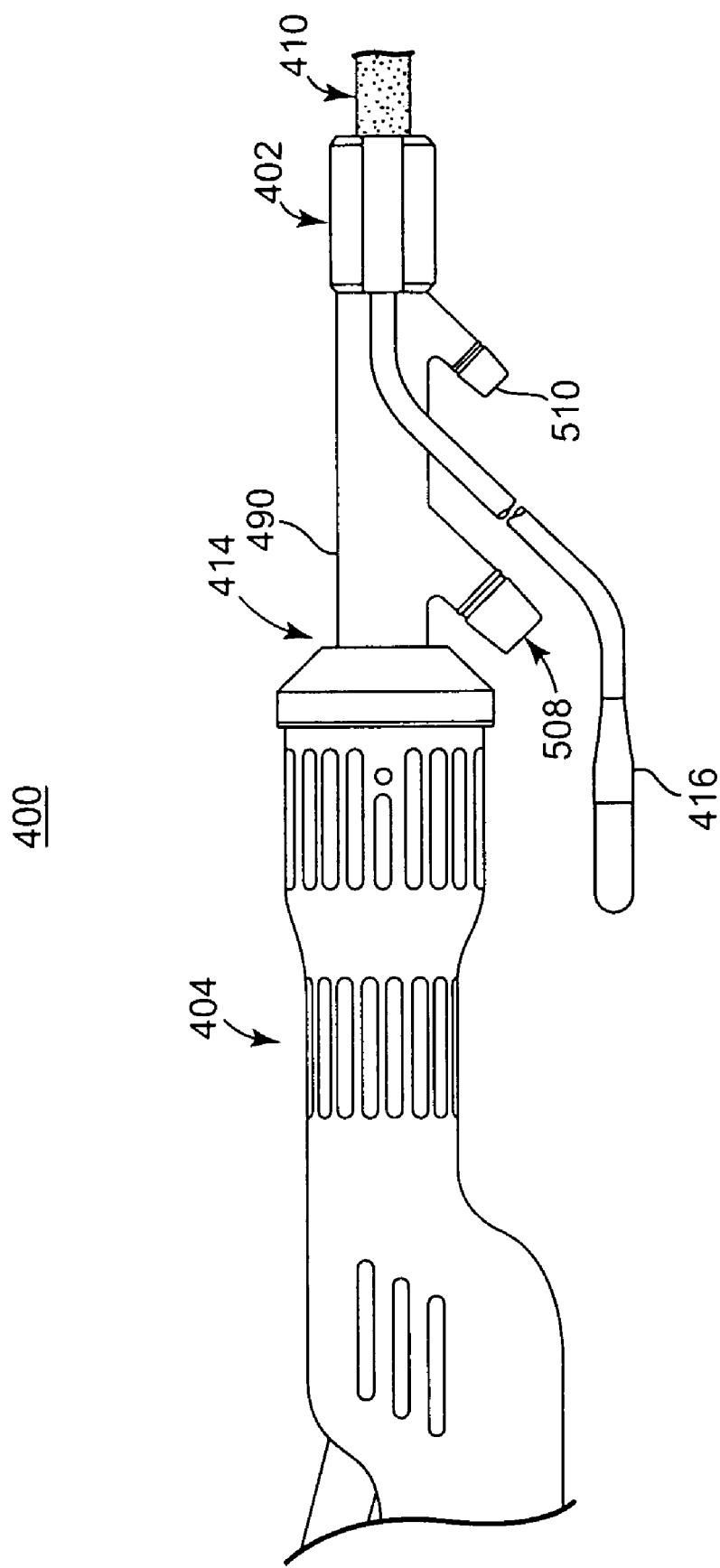
FIG. 11 is an enlarged side view of portions of the instrument and motorized handpiece of FIG. 8 assembled to one another.

Prior to use, and returning to FIG. 8, the surgical micro-resecting instrument 402 is assembled to the motorized handpiece 404. The motorized handpiece 404 can again assume a wide variety of forms, and is generally assembled to the surgical micro-resecting instrument 402 by capturing portions of the first and second hubs 490, 492. One example of this relationship is shown in FIG. 11 (it being understood that in the view of FIG. 11, the second hub 492 is entirely encompassed within the motorized handpiece 404). Notably, while the motorized handpiece 404 contacts/engages the first and second hubs 490, 492, the outer and inner members 410, 412 are electrically isolated or insulated from the motorized handpiece 404 via the non-conductive nature of the hub assembly 414. Thus, the hub assembly 414 serves as a non-conductive coupling body for assembly that electrically isolates the motorized handpiece 404 from the electrical pathway established by the micro-resecting instrument 402.

Returning to FIG. 8, the wiring 416 is connected to the evoked potential monitoring device 406. In particular, and as previously described, an energy source (not shown) associated with the evoked potential monitoring device 406 is electrically connected to the wiring 416 such that electrical energy generated by the energy source is conducted through the wiring 416 and thus, through the electrical pathway to the probe surface 560. The evoked potential monitoring device 406 can further be electronically coupled to the motorized handpiece 404, with the evoked potential monitoring device 406 being programmed to disable the motorized handpiece 404 in response to certain sensed events as described below.

During use, the system 400 operates in a manner highly similar to that described above with respect to the system 330 (FIG. 7). As part of a micro-resecting procedure, a user directs the cutting window 438 toward a target site (for example, as part of an endoscopic procedure). In connection with this placement, an evoked potential monitoring procedure can be performed to evaluate a proximity of the probe surface 560, and thus of the cutting window 438/cutting tip 480 (FIGS. 9 and 10) relative to a bodily site or structure of interest (e.g., nerves). In particular, the evoked potential monitoring device 406 prompts delivery (preferably continuous delivery) of a stimulation energy (e.g., current) through the wiring 416 to the probe surface 560 via the electrical pathway established by the micro-resecting instrument 402. Properly placed patient electrodes (not shown) provide the evoked potential monitoring device 406 with information indicative of a proximity of the probe surface 560 (and thus of the cutting window 438/cutting tip 480) relative to the bodily structure of interest (e.g., nerves) in response to the applied stimulation energy. For example, based upon a comparison of the applied stimulation energy with the signaled information from the patient electrodes, the evoked potential monitoring device 406 can detect, and/or provide the user with information indicative of, the probe surface 560 (and thus, the cutting window 438/cutting tip 480) being at or within a close proximity of the bodily structure of concern.

Once the user is confident that the cutting window 438 is safely away from nerves (or other bodily site or structure of interest), the motorized handpiece 404 is operated to perform a micro-resecting procedure at the target site, whereby the inner member 412 (FIGS. 9 and 10) is rotated/oscillated relative to the outer tubular member 410 such that contacted bone, tissue, or other bodily material in contact with the cutting tip 480 (FIGS. 9 and 10) at the cutting window 438 is resected. During the micro-resection operation, the evoked potential monitoring device 406 can be operated to continuously evaluate a proximity of the probe surface 560 relative to nerves or other bodily structures of sites of interest. Further, in some embodiments, the evoked potential monitoring device 406 is adapted and programmed to produce an alarm (visual, audible, or both) to the user in the event the probe surface 560 is sensed to be in close proximity to a nerve (or other bodily structure). In other embodiments, the evoked potential monitoring device 406 is adapted and programmed to automatically disable the motorized handpiece 404 upon determining that the probe surface 560 is in close proximity to the bodily site/structure of interest.

Where desired, the surgical target site and/or the cutting window 438 can be irrigated via fluid supplied from an irrigation source (not shown) to the irrigation port 510 and thus to the cutting window 438. Similarly, resected bodily material can be aspirated from the target site via application of a vacuum (not shown) on the aspiration port 508 that is otherwise fluidly connected to the cutting tip 480 (FIGS. 9 and 10).

While operation of the system 400 has been described with reference to procedures in which a proximity of the probe surface 560 relative to nerves is evaluated or detected (for example as part of an ENT surgical procedure (e.g., sinus surgery), intervertebral disc procedures, etc.), a variety of other surgical procedures can also benefit from the system 400 that otherwise provides evoked potential monitoring. For example, the system 400 can be used as part of an ocular surgical procedure in which the evoked potential monitoring device 406 can be used to detect whether the probe surface 560 (and thus the cutting window 438/cutting tip 480) has broken through the thin or brittle bone. In particular, the evoked potential monitoring device 406 can detect, via a rapid drop in tissue impedance, that the orbital bone has been compromised. Under these circumstances, the evoked potential monitoring device 406 can be configured to immediately disable operation of the motorized handpiece 404 so as to prevent possible patient harm.

Regardless of the particular surgical procedure with which the system 400 is employed, performance of the evoked potential monitoring operation is characterized by a low level stimulation energy being provided to the probe surface 560. In particular, only a low level stimulation energy (on the order of 0.01 mA-30.0 mA) is required, and is selected so as to not cause cauterization of human tissue. Thus, in some embodiments, the energy source associated with the evoked potential monitoring device 406 does not deliver RF energy that might otherwise cause tissue cauterization at the probe surface 560.

Figure 12:
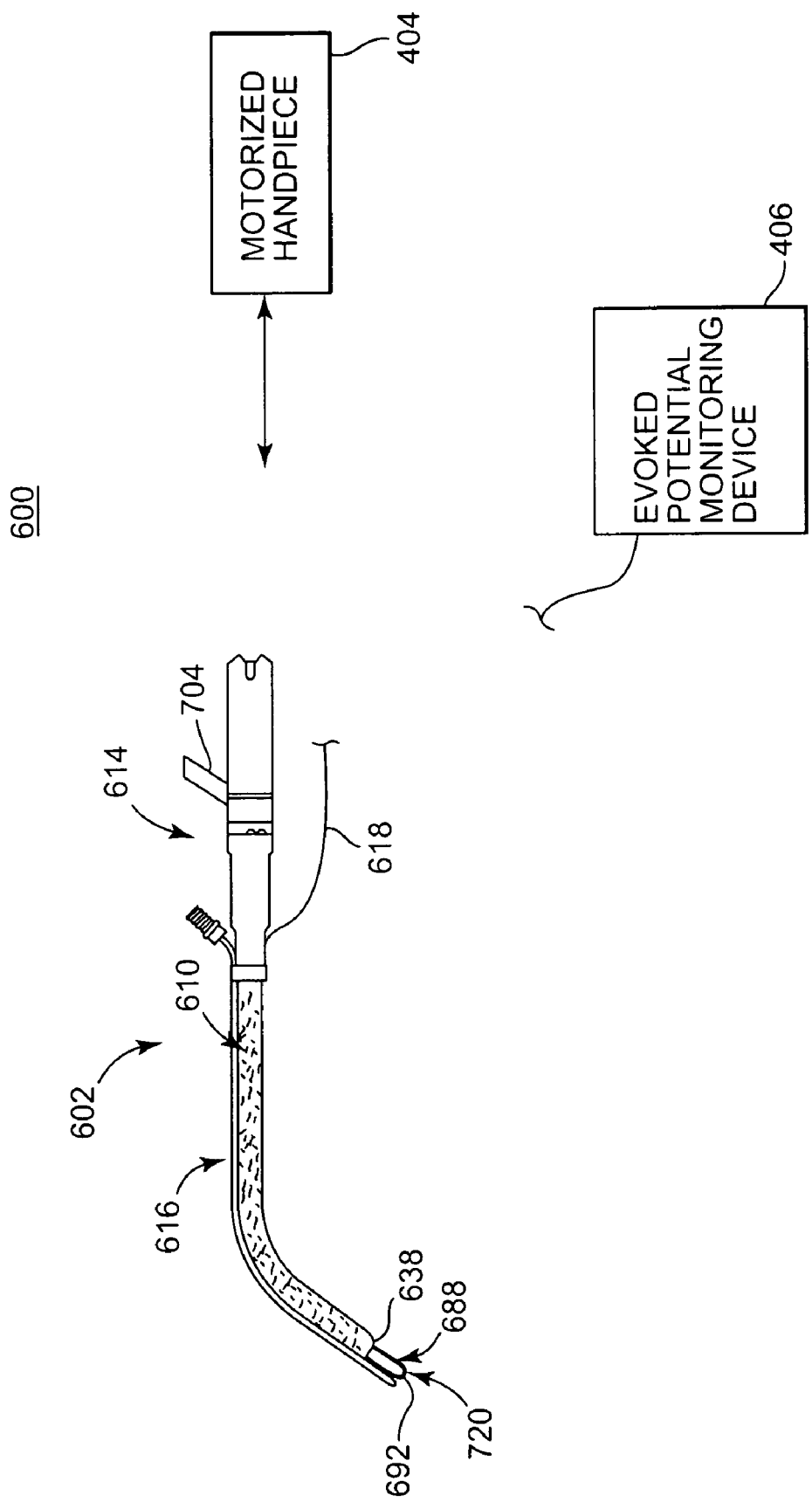
FIG. 12 is a schematic illustration, with portions shown in block form, of another surgical cutting system in accordance with principles of the present invention and incorporating a surgical micro-resecting instrument.

Another surgical micro-resecting system 600 in accordance with aspects of the present invention is shown in FIG. 12. The system 600 is similar to the system 400 (FIG. 8) previously described, and includes a micro-resecting instrument 602, the motorized handpiece 404, and the evoked potential monitoring device 406. With additional reference to FIG. 13, the micro-resecting instrument 602 is similar to the instrument 402 (FIG. 8), and general includes an outer tubular member 610, an inner member 612, a hub assembly 614, an irrigation assembly 616, and wiring 618. The inner member 612 is coaxially disposed within the outer tubular member 610, and in one embodiment is tubular. The hub assembly 614 maintains the outer and inner members 610, 612 so as to facilitate rotation of the inner member 612 via the motorized handpiece 404. The irrigation assembly 616 provides an irrigation pathway from an irrigation source (not shown). The wiring 618 electrically connects the micro-resecting instrument 602 to the evoked potential monitoring device 406, and in particular an energy source (not shown) thereof. In this regard, the hub assembly 614 serves as a non-conductive coupling, electrically isolating the micro-resecting instrument 602 from the motorized handpiece 404.

Figure 13:
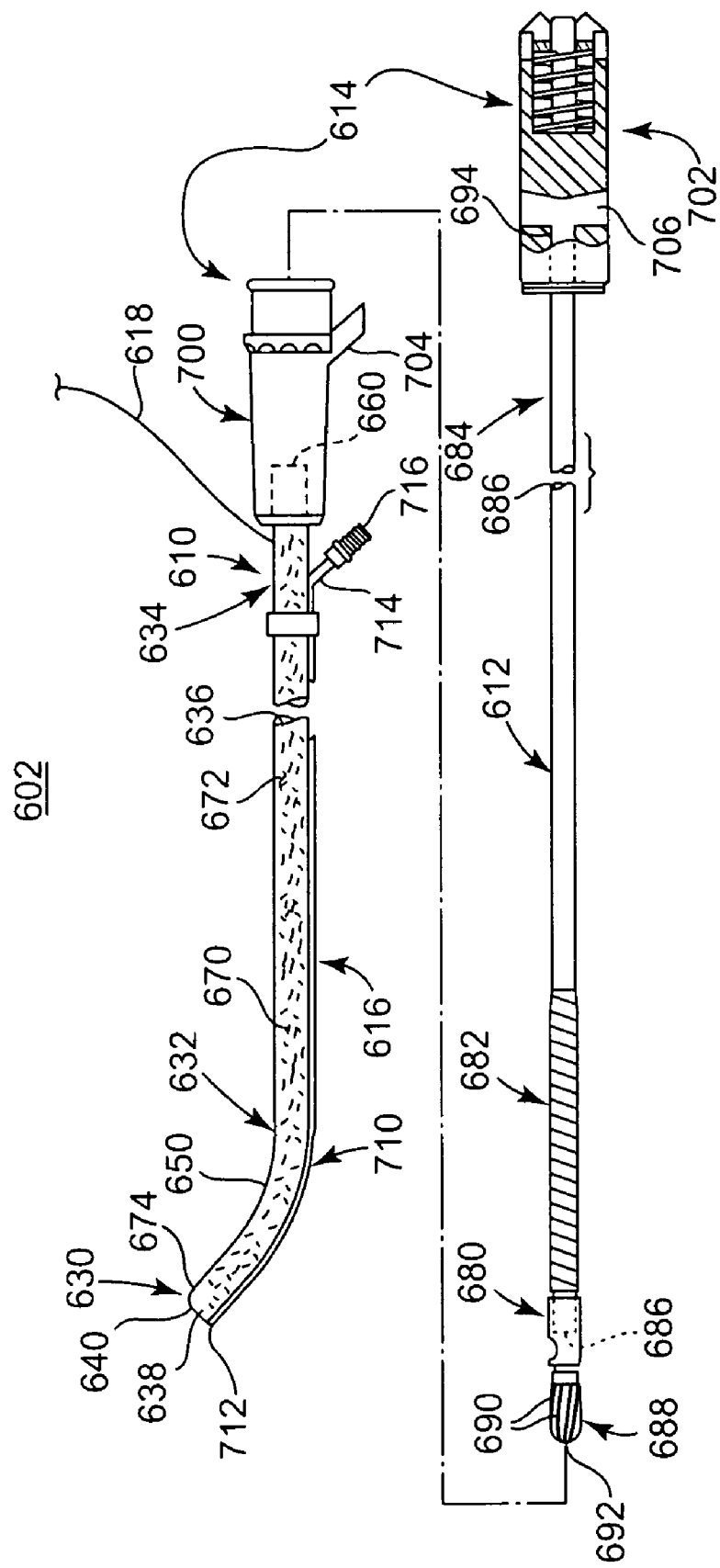
FIG. 13 is an exploded view of the micro-resecting instrument of FIG. 12.

With specific reference to FIG. 13, the outer tubular member 610 is similar in many respects to the outer tubular member 410 (FIG. 8) previously described, and generally defines a distal section 630, an intermediate section 632, and a proximal section 634. A lumen 636 extends from the distal section 630 to the proximal section 634, with the distal section 630 forming a cutting window 638 that is otherwise fluidly open to the lumen 636. In some embodiments, the cutting window 638 extends to a distal end 640 of the outer tubular member 610 such that the distal end 640 is radially open to the lumen 636. In other embodiments, a tip (not shown) is further provided, extending distal the cutting window 638.

The intermediate section 632 extends from the distal section 630 and, with the one embodiment of FIGS. 12 and 13, forms a bend 650. Once again, the bend 650 can assume a wide variety of forms or angles, and multiple bends can be defined. Conversely, the outer tubular member 610 can be linear or straight along an entire length thereof.

The proximal section 634 is configured to be maintained by the hub assembly 614, and terminates at a proximal end 660.

The outer tubular member 610 is formed of an electrically conductive material (e.g., stainless steel) and is electrically coupled to the wiring 618 at the proximal section 634. As a point of reference, FIGS. 12 and 13 illustrate the outer tubular member 610/wiring 618 interface as being exposed, distal the hub assembly 614. In a non-limiting more preferential construction, the interface is exteriorly covered, such as by overmolding the wiring 618 within a component of the hub assembly 614, providing a separate cap/cover (e.g., akin to the cap 542 of FIG. 9), etc. Regardless, a dielectric insulation or electrically non-conductive material 670 (shown with stippling in FIGS. 12 and 13) is applied to an exterior surface 672 (referenced generally) of the outer tubular member 610 along the intermediate section 632 and at least a portion of the distal section 630. The exterior surface 672 along a distal region 674 of the distal section 630 can remain exposed, as well as along the proximal section 634. With this configuration, then, electrical energy provided by the wiring 618 is applied to the proximal section 634 and conducted along the outer tubular member 610. The non-conductive material 670 electrically insulates the outer tubular member 610 except at the exposed distal region 674. Alternatively, an entirety of the distal section 630 is encompassed by the non-conductive material 670.

The inner member 612 is similar to the inner member 412 (FIG. 8) previously described, and includes a distal portion 680, an intermediate portion 682, a proximal portion 684, and a lumen 686 (with configurations in which the inner member 512 is tubular). The distal portion 680 forms or includes a cutting tip 688 that, in the one embodiment of FIG. 13, is a bur head including teeth 690. The cutting tip 688 forms a central opening 692 (referenced generally) that is fluidly connected to the lumen 686. With this configuration, then, materials can be aspirated through the opening 692 via application of a vacuum on the lumen 686. In this regard, the lumen 686 is also open at a proximal end 694 of the inner member 612. The inner member 612 can have a varying construction (e.g., the intermediate portion 682 is flexible, whereas the distal and proximal portions 680, 684 are rigid), however, the inner member 612 as a whole is electrically conductive.

The hub assembly 614 is in many respects similar to the hub assembly 414 (FIGS. 8 and 9) previously described, and includes a first hub 700 and a second hub 702. In general terms, the hubs 700, 702 are formed of an electrically non-conductive material (e.g., plastic) such that the hub assembly 614 electrically isolates the outer and inner members 610, 612 from the motorized handpiece 404 (FIG. 12) upon final assembly. With this in mind, the first hub 700 serves as an outer hub, and is configured for assembly over the proximal section 634 of the outer tubular member 610, as well as to coaxially receive and maintain the second hub 702. The outer hub 700 can form an aspiration port 704 that is otherwise fluidly connected to a passageway (not shown) formed within the outer hub 700. The second hub 702 serves as an inner, rotatable hub, and is adapted for assembly to the proximal portion 684 of the inner member 612, as well as to be rotatably received within the first hub 700. The second hub 702 can form an aspiration passage 706 that, upon final assembly of the first and second hubs 700, 702, is fluidly connected to the aspiration port 704.

Finally, the irrigation assembly 616 includes, in some embodiments, an irrigation tube 710 extending from an open, distal end 712 to a proximal end 714 that is fluidly connected to and/or forms a coupling 716. The irrigation tube 710 can be formed of a rigid yet malleable material to facilitate assembly thereof to the outer tubular member 610. In this regard, the irrigation tube 710 conforms to the bend 650, with the distal end 712 being positioned at or adjacent the cutting window 638. The coupling 716 is appropriately configured for fluid connection to a supply tube (not shown) otherwise associated with an irrigation supply source (not shown). With this configuration, then, the irrigation assembly 616 establishes an irrigation pathway from the irrigation source to the distal end 712.

Upon final assembly, the inner member 612 is rotatably disposed within the outer tube 610 such that the cutting tip 688 is exteriorly exposed at the cutting window 638. The inner hub 702 is secured to the inner member 612 and is rotatably maintained by the outer hub 700, with the outer hub 700 retaining the outer tubular member 610. As such, rotation of the inner hub 702 relative to the outer hub 700 results in rotation of the cutting tip 688 at or within the cutting window 638. Further, an aspiration pathway is established from the opening 692 of the cutting tip 688 to the aspiration port 704. Finally, an electrical pathway is established by the micro-resecting instrument 602 from the wiring 618 to a probe surface 720 (referenced generally in FIG. 12) otherwise defined at or adjacent the cutting window 638. In some embodiments, the exposed distal region 674 of the outer tubular member 610 serves as at least a portion of the probe surface 720. In other embodiments, the intimate metal-to-metal contact between the outer and inner members 610, 612 allows for conduction of electrical energy from the outer tubular member 610 to the inner member 612, and thus to the cutting tip 688. To account for the possibility that during high-speed operation, there may be instances of time where there is no direct contact between the outer and inner members 610, 612, an electrically conductive grease can be provided between the members 610, 612 to ensure continuous electrical continuity. Regardless, the cutting tip 688 can thus also serves as part of the probe surface 720. In fact, where an entirety of the distal section 630 of the outer tubular member 610 is encompassed by the non-conductive material 670, the cutting tip 688 is the probe surface 720.

During use, the system 600 operates in a manner highly similar to that previously described with respect to the system 400 (FIG. 8). In particular, the motorized handpiece 404 is operated to cause rotation of the cutting tip 688 within the cutting window 638. Periodically during and/or simultaneous with a micro-resecting procedure, evoked potential monitoring can also be performed via operation of the evoked potential monitoring device 406 to evaluate a proximity of the probe surface 720, and thus of the cutting window 638/cutting tip 688, relative to a bodily structure or site of concern. In particular, the energy source (not shown) associated with the evoked potential monitoring device 406 is prompted to deliver a stimulation energy through the wiring 618 and thus to the probe surface 720. A sensed patient reaction to this stimulation energy (e.g., via patient probes as previously described) is employed by the evoked potential monitoring device 406 to evaluate a proximity of the probe surface 720, and thus of the cutting window 638/cutting tip 688 relative to a bodily structure of interest (e.g., nerves). This evaluation can be performed periodically or continuously, and in some embodiments, the evoked potential monitoring device 406 is adapted or programmed to warn a user of a potentially dangerous resecting location and/or automatically disable the handpiece 404.

Where desired, the target or surgical site can be irrigated via delivery of an irrigation fluid through the irrigation tube 710. The so-delivered irrigation fluid is dispensed at or adjacent the cutting window 638. Similarly, material(s) at the surgical or target site can be aspirated therefrom via application of a vacuum onto the aspiration port 704 that in turn draws the material through the opening 692 at the cutting tip 688.

In light of the above, the advantages of non-sequential, high-speed cutting and probing or other monitoring can be realized in accordance with embodiments of the present invention. The surgical cutting instrument and related surgical cutting system can be employed to perform virtually any surgical procedure requiring cutting of tissue and nerve or other tissue monitoring, and especially with those procedures in which a small diameter, cutting tip is rotated at elevated speeds to effectuate desired tissue resection in an otherwise confined surgical access site. For example, the instrument and system of embodiments of the present invention can be employed to perform procedures such as sinus surgery, intervertebral disc surgery, ocular surgery, etc., to name but a few. Aspects of the present invention are not limited to any particular procedure, cutting tip style, or cutting speed. Regardless of the exact procedure, the instrument and system of embodiments of the present invention operate to provide both tissue cutting and evoked potential (i.e., nerve) monitoring without the need for a separate electrical probe instrument.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A method of performing a surgical micro-resecting procedure at a target site of a patient, the method comprising:
    providing a micro-resecting instrument including:
        an outer tubular member having a lumen, a proximal section, and a distal section forming a cutting window fluidly connected to a lumen,
        an inner member disposed within the lumen and having a proximal portion and a distal portion, the distal portion including a cutting tip positioned at the cutting window upon final assembly,
        a hub assembly maintaining the proximal section and the proximal portion,
        an electrically non-conductive material covering a region of the outer tubular member distal the hub assembly,
        wiring electrically connected to the outer tubular member,
        wherein the instrument defines a probe surface proximate the cutting window, the probe surface characterized by the absence of the non-conductive material,
        and further wherein an electrical pathway is established from the wiring to the probe surface,
    electrically connecting the wiring to an evoked potential monitoring device such that an energy source of the evoked potential monitoring device is in electrical communication with the probe surface;
    delivering the distal section of the outer tubular member toward the target site such that the cutting window is adjacent the target site;
    applying a stimulation energy to the probe surface via the energy source and the wiring;
    operating the evoked potential monitoring device to evaluate a proximity of the probe surface relative to a bodily structure of interest based upon reference to the applied stimulation energy;
    rotating the inner member relative to the outer tubular member to perform a micro-resecting operation in which bodily material at the target site is resected by the cutting tip within the cutting window; and attaching a motorized handpiece to the hub assembly such that operation of the handpiece causes the inner member to rotate relative to the outer tubular member, and further wherein the hub assembly electrically isolates the micro-resecting instrument from the handpiece.

2. The method of claim 1, wherein the evaluation of a proximity of the probe surface relative to a bodily structure of interest is indicative of a proximity of the cutting window relative to the bodily structure of interest.

3. The method of claim 1, wherein delivering the distal section toward the target site includes:
    simultaneously performing evoked potential monitoring with movement of the distal section, whereby as the distal end is moved toward the target site, stimulation energy is delivered to the probe surface for evaluating a proximity of the probe surface relative to a bodily structure of interest.

4. The method of claim 1, wherein the micro-resecting operation and the proximity evaluation are performed simultaneously.

5. The method of claim 1, wherein rotating the inner member to perform a micro-resecting operation includes:
    rotating the inner member for a first period of time;
    applying a stimulation energy to the probe surface upon completion of the first period of time as part of a proximity evaluation; and
    determining whether to rotate the inner member for a second period of time based upon the proximity evaluation.

6. The method of claim 1, further comprising:
    automatically stopping rotation of the inner member based upon the evaluated proximity.

7. The method of claim 1, wherein the bodily structure of interest is a nerve.

8. The method of claim 1, wherein the bodily structure of interest is an ocular bone.

9. The method of claim 1, wherein the method is performed as part of an endoscopic procedure.

10. The method of claim 1, wherein the outer tubular member includes a curved region distal the hub assembly.

11. The method of claim 1, wherein the applied stimulation energy is characterized as not being RF energy.

12. The method of claim 1, wherein applying a stimulation energy is characterized by the absence of tissue cauterization at the target site.

13. The method of claim 1, wherein the probe surface is defined at least in part by an exposed distal region of the outer tubular member.

14. The method of claim 1, wherein the probe surface is defined at least in part by the cutting tip.

15. The method of claim 1, wherein the inner member forms a central lumen and an opening to the central lumen at the cutting tip, the method further comprising:
    aspirating material from the target site through the opening and the central lumen.

16. A surgical micro-resecting system comprising:
    a micro-resecting instrument including:
        an outer tubular member having a lumen, a proximal section, and a distal section forming a cutting window fluidly connected to the lumen,
        an inner member disposed within the lumen and having a proximal portion and a distal portion including a cutting tip positioned at the cutting window upon final assembly,
        a hub assembly maintaining the proximal section and the proximal portion,
        an electrically non-conductive material covering a region of the outer tubular member distal the hub assembly,
        wiring electrically connected to the outer tubular member,
        where the instrument defines a probe surface proximate the cutting window, the probe surface characterized by the absence of the non-conductive material,
        and further wherein an electrical pathway is established from the wiring to the probe surface;
    a motorized handpiece selectively coupled to the hub assembly for rotating the inner member relative to the outer tubular member wherein the hub assembly is configured to electrically isolate the micro-resecting instrument from the motorized handpiece; and
    an evoked potential monitoring device having an energy source selectively coupled to the wiring for applying a stimulation energy to the probe surface via the wiring and configured to evaluate a proximity of the probe surface relative to a bodily structure of interest.

17. The system of claim 16, wherein the outer tubular member is curved along a length thereof distal the hub assembly.

18. The system of claim 16, wherein the motorized handpiece is electronically coupled to the evoked potential monitoring device and further wherein the evoked potential monitoring device is adapted to prompt disablement of the motorized handpiece based upon an evaluated proximity of the probe surface relative to a bodily structure of interest.

19. The system of claim 16, wherein the energy source is characterized as generating a low level stimulation energy that is not capable of cauterizing human tissue.

20. The system of claim 16, wherein the cutting window includes a plurality of teeth.

21. The system of claim 16, wherein the cutting tip includes a plurality of cutting teeth arranged about a mouth.

22. The system of claim 16, wherein the cutting tip is a bur.

23. The system of claim 16, wherein the probe surface is defined at least in part by an exposed distal region of the outer tubular member.

24. The system of claim 16, wherein the probe surface is defined at least in part by the cutting tip.

25. The system of claim 16, further comprising:
an irrigation pathway terminating adjacent the cutting window; and
an irrigation source fluidly connected to the irrigation pathway.

26. The system of claim 25, wherein the irrigation pathway is formed between the inner and outer tubular members.

27. The system of claim 25, wherein the irrigation pathway includes a tube assembled to an exterior of the outer tubular member.

28. The system of claim 16, wherein the instrument further includes an electrical coupling establishing a continuous electrical communication between the wiring and the inner tubular member.

29. The system of claim 16, wherein the inner member is tubular, defining a central lumen.

* * * * *

UNITED STATES PATENT AND TRADEMARK OFFICE
CERTIFICATE OF CORRECTION

| | | |
|---|---|---|
| PATENT NO. | : 8,016,846 B2 | Page 1 of 1 |
| APPLICATION NO. | : 11/446520 | |
| DATED | : September 13, 2011 | |
| INVENTOR(S) | : David Reinker and Kevin McFarlin | |

It is certified that error appears in the above-identified patent and that said Letters Patent is hereby corrected as shown below:

Column 27, line 2, delete "perfouning" and insert --performing--.

Column 28, line 26, delete "folins" and insert --forms--.

Signed and Sealed this
Tenth Day of January, 2012

David J. Kappos
*Director of the United States Patent and Trademark Office*